United States Patent [19]

Cover et al.

[11] Patent Number: 5,403,924
[45] Date of Patent: Apr. 4, 1995

[54] TAGA GENE AND METHODS FOR DETECTING PREDISPOSITION TO PEPTIC ULCERATION

[75] Inventors: Timothy L. Cover; Murali K. R. Tummuru; Martin J. Blaser, all of Nashville, Tenn.

[73] Assignee: Vanderbilt University, Nashville, Tenn.

[21] Appl. No.: 53,614

[22] Filed: Apr. 26, 1993

Related U.S. Application Data

[63] Continuation-in-part of Ser. No. 959,940, Oct. 13, 1992, abandoned.

[51] Int. Cl.[6] .................. C07H 21/02; C07H 21/04
[52] U.S. Cl. ..................... 536/23.1; 536/23.7
[58] Field of Search ............... 536/23.1, 23.7; 435/320.1, 240.2

[56] References Cited

PUBLICATIONS

Prewett et al., Gastroenterology 102:829-833 (1992) "DNA patterns of Helicobacter pylori isolated"...
Tummuru et al., Astr. Gen. Meet. Am. Soc. Microbiol "Molecular cloning of a unique antigen"...
Labigne et al., J. Bact. 173:1920-1931 (1991) "Shuttle cloning and nucleotide sequences"...
Xiang et al. Lancet i:900-901, 1993.
Crabtree et al., J. Clin. Pathol. 45:733-734, 1992.
Gerstenecker et al. Eur. J. Clin. Microbiol. Infect. Dis., 11(7):595-601, Jul. 1992.
Timothy L. Cover and Martin J. Blaser J. Biol. Chemistry, 267(15):10570-10575, May 1992.
Crabtree et al., J. Clin. Pathol., 45:733-734, 1992.
Cover et al., J. Clin. Investigation 90:001-006, 1992.
Crabtree et al. Digestive Diseases & Sciences, 36(9):1266-1273, Sep. 1991.
Crabtree et al. The Lancet, vol. 338:332-335, Aug., 1991.
Cover et al., Infect. & Immunity, 59(4):1264-1270, Apr. 1991.
Cover et al. Infect. & Immunity, 58(3):603-610, 1990.
Hirschl et al., J. Clin. Pathol, 43:511-513, 1990.
Figura et al., J. Clin. Microbio. 27(1):225-226, 1989.
Leunk et al. J. Med. Microbiol. 26:93-99, 1988.
Apel et al. Zbl. Bakt. Hyg., A268:271-276, 1988.
Wulffen et al. J. Clin. Pathol., 41:653-659, 1988.

Primary Examiner—Margaret Parr
Assistant Examiner—Eggerton Campbell
Attorney, Agent, or Firm—Needle & Rosenberg

[57] ABSTRACT

The present invention provides an isolated nucleic acid encoding an approximately 120–128 kilodalton antigen of Helicobacter pylori, or an antigenic fragment thereof, wherein the antigen is associated with peptic ulceration. The present invention also provides methods of detecting the presence of a Helicobacter pylori strain possessing the 120–128 kilodalton antigen in a subject, comprising the steps of contacting an antibody-containing sample from the subject with a detectable amount of the tagA antigen or antigenic fragment of the present invention and detecting the reaction of the antigen or fragment and the antibody. A mutant H. pylori not expressing a functional tagA antigen is also provided.

6 Claims, 3 Drawing Sheets

TAGA GENE AND METHODS FOR DETECTING PREDISPOSITION TO PEPTIC ULCERATION

BACKGROUND OF THE INVENTION

This application is a continuation-in-part of application Docket 2200.006, Ser. No. 07/959,940, filed Oct. 13, 1992, now abandoned.

*Helicobacter pylori* is now recognized as an important pathogen of humans in that the chronic gastritis it causes is a risk factor for the development of peptic ulcer disease and adenocarcinoma of the stomach. However, although essentially all infected persons develop gastritis, clinical consequences of *H. pylori* infection are recognized in only a minority of persons.

One explanation for this diversity of outcomes is that *H. pylori* strains may be heterogeneous. At a genetic level, *H. pylori* strains show a high degree of diversity, but most phenotypic characteristics are well-conserved. Two exceptions to the phenotypic homogeneity are currently recognized. First, about 50%-60% of *H. pylori* strains produce a vacuolating cytotoxin in vitro (Cover et al. *Infect. Immun.* 58:603-610, 1990; Leunk et al. *J. Med. Microbiol.* 26:93-99,1988), and toxin production is associated with peptic ulceration (Figura et al. *J. Clin. Microbiol.* 27:225-226, 1988). Second, there is heterogeneity in whether an antigenic protein migrating at approximately 120-128 kilodalton (kDa) on reducing sodium dodecyl sulfate-polyacrylamide gel electrophoresis [SDS-PAGE] is produced (Cover et al. 58:603-610, 1990). Although toxic activity is mediated by an 87 kDa protein (Cover and Blaser *J. Biol. Chem.* 267:10570-10575, 1992; Cover et al. *J. Clin. Invest.* 90: 913-918, 1992), toxin production itself is associated with the presence of the antigenic 120-128 kDa protein (Cover et al., 1990). Previous studies have found that about 60-80% of *H. pylori* isolates express the 120-128 kDa protein (Apel et al. *Zbl. Bakt. Hyg. A.* 268:217-276, 1988; Cover et al., 1990). Notably, presence of antibodies to the 120-128 kDa protein in either serum or mucosal secretions is associated with the presence of peptic ulceration (Cover et al. 1990; Crabtree et al. *Lancet* 338:332-335).

Until now, little was known about the association between toxin production and the 120-128 kDa antigen. This is due to the previous inability to further characterize the 120-128 kDa antigen after its initial visualization.

In previous studies, the 120-128 kDa antigen was visualized by Western blotting, but virtually no other characterization was performed (Cover et al., 1990). In contrast to the ease with which this antigen has been visualized by Western blotting, the 120-128 kDa band has not been easily visualized by other methods such as silver staining (FIG. 2 in Cover et al., 1990). The explanation for this phenomenon is that this antigen is present only in minute quantities, relative to other *H. pylori* proteins. Recently, Gerstenecker et al. (*Eur. J. Clin. Microbiol. Infect. Dis.* 11(7):595-601, 1992) have reported the isolation of an approximately 120 kDa protein from *H. pylori* which reacts with positive human control serum. However, virtually no characterization (such as N-terminal sequencing) of this antigen has been performed.

Despite the difficulty of purification, the present invention provides the cloning and sequence of the gene and deduced amino acid sequence encoding the 120-128 kDa protein. This data was obtained using alternate methodology that did not require purification of the 120-128 kDa antigen. The invention also provides diagnostic, therapeutic, and prophylactic compositions and methods.

SUMMARY OF THE INVENTION

The present invention provides an isolated nucleic acid encoding an approximately 120-128 kilodalton antigen of *Helicobacter pylori*, or an antigenic fragment thereof, wherein the antigen is associated with peptic ulceration. The present invention also provides methods of detecting the presence of a *Helicobacter pylori* strain possessing the 120-128 kilodalton antigen in a subject, comprising the steps of contacting an antibody-containing sample from the subject with a detectable amount of the tagA antigen or fragment thereof of the present invention and detecting the reaction of the fragment and the antibody.

DETAILED DESCRIPTION OF THE INVENTION

Nucleic Acids

Figure 1:
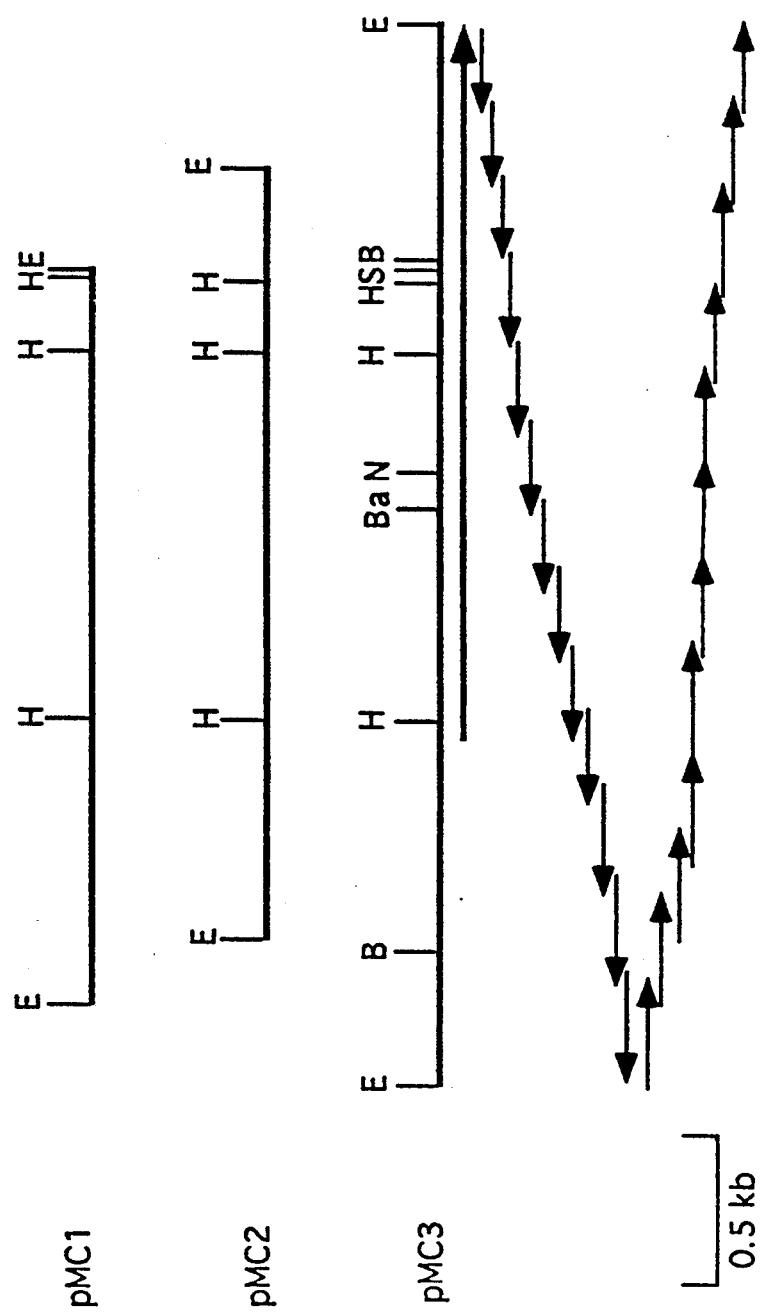
FIG. 1 shows physical maps of plasmids pMC1, pMC2, and pMC3. The large arrow beneath pMC3 represents the location of the tagA gens and the direction of transcription as determined by deletion mutations and immunoblotting. The small arrows represent the strand and extent of DNA sequenced from exonuclease III-derived fragments. Restriction endonuclease cleavage sites: B, BglII; Ba, BamHI; E, EcoRI; H, HindIII; N, NdeI; S, SacI.

The present invention provides an isolated nucleic acid encoding an approximately 120-128 kDa antigen or fragment of *H. pylori*, associated with peptic ulceration. By "isolated" is meant separated from other nucleic acids found in the naturally occurring organism. The nucleic acid encoding the 120-128 kDa antigen is specific for *H. pylori* expressing the 120-128 kDa antigen. By "specific" is meant an isolated sequence which does not hybridize with other nucleic acids to prevent an adequate positive hybridization with nucleic acids from *H. pylori* possessing the antigen. Specifically, an example of such a nucleic acid is an open reading frame of 3543 base pairs comprising nucleotides 1072 through 4614 contained in a 4821 base pair insert (SEQ ID NO:3). A cell line containing a plasmid having the full length tagA gene is deposited with the American Type Culture Collection (1230 Parklawn Drive, Rockville, Md. 20852) under ATCC Accession No. 69273. This specific nucleic acid can be used to detect *H. pylori* possessing the 120–128 kDa antigen in methods such as polymerase chain reaction, ligase chain reaction and hybridization. Alternatively, the 4821 base pair sequence can be utilized to produce the full length tagA protein.

Another example of such a nucleic acid is a truncated open reading frame of 2577 base pairs comprising nucleotides 1072 through 3648 contained in a 3648 base pair insert (SEQ ID NO:1). This specific nucleic acid can be used to detect *H. pylori* possessing the 120–128 kDa antigen in methods such as polymerase chain reaction, ligase chain reaction and hybridization. Alternatively, the 3648 base pair sequence can be utilized to produce a truncated protein.

In addition, the nucleic acid can be homologous with nucleotide sequences present in other bacteria. Such an amino acid sequence shared with other bacteria can be used for example to simultaneously detect related strains or as a basis for a multiprotective vaccine.

An isolated nucleic acid capable of selectively hybridizing with or selectively amplifying a nucleic acid encoding the 120–128 kDa antigen or fragments thereof is also contemplated. An isolated nucleic acid complementary to the above nucleic acid is also provided. The sequences can be selected based on the nucleotide sequence and the utility of the particular sequence.

Modifications to the nucleic acids of the invention are also contemplated as long as the essential structure and function of the polypeptide encoded by the nucleic acids is maintained. Likewise, fragments used as primers or probes can have substitutions so long as enough complementary bases exist for selective hybridization (Kunkel et al. *Methods Enzymol.* 1987:154:367, 1987).

Antigen

Purified antigenic polypeptide fragments encoded by the nucleic acids of the present invention are also contemplated. As used herein, "purified" means the antigen is sufficiently free of contaminants or cell components with which the antigen normally occurs to distinguish the antigen from the contaminants or components. The purified approximately 120–128 kDa full-length antigen, truncated antigen and antigenic fragments of the present invention are also referred to herein as "the antigen" or "the tagA antigen."

Specifically, an approximately 130 kDa full length tagA antigenic polypeptide (SEQ ID NO:4) is encoded by an open reading frame of 3543 base pairs within the 4821 base pair cloned insert, consisting essentially of the amino acids encoded by nucleotides 1072 through 4614 contained in the nucleotide sequence defined in the Sequence Listing as SEQ ID NO:3.

Additionally, an approximately 96 kDa antigenic polypeptide is encoded by an open reading frame of 2577 base pairs within the 3648 base pair cloned insert, consisting essentially of the amino acids encoded by nucleotides 1072 through 3648 contained in the nucleotide sequence defined in the Sequence Listing as SEQ ID NO:1.

An antigenic fragment of the antigen can be isolated from the whole antigen or truncated antigen by chemical or mechanical disruption. The purified fragments thus obtained can be tested to determine their antigenicity and specificity by the methods taught herein. Antigenic fragments of the antigen can also be synthesized directly. An immunoreactive fragment is defined as an amino acid sequence of at least about 5 consecutive amino acids derived from the antigen amino acid sequence.

The polypeptide fragments of the present invention can also be recombinant proteins obtained by cloning nucleic acids encoding the polypeptide in an expression system capable of producing the antigenic polypeptide or fragments thereof.

Once the amino acid sequence of the antigen is provided, it is also possible to synthesize, using standard peptide synthesis techniques, peptide fragments chosen to be homologous to immunoreactive regions of the antigen and to modify these fragments by inclusion, deletion or modification of particular amino acids residues in the derived sequences. Thus, synthesis or purification of an extremely large number of peptides derived from the antigen is possible.

The amino acid sequences of the present polypeptides can contain an immunoreactive portion of tagA antigen attached to sequences designed to provide for some additional property, such as solubility. The amino acid sequences of an tagA antigen can include sequences in which one or more amino acids have been substituted with another amino acid to provide for some additional property, such as to remove/add amino acids capable of disulfide bonding, to increase its bio-longevity, alter enzymatic activity, or alter interactions with gastric acidity. In any case, the peptide must posses a bioactive property, such as immunoreactivity, immunogenicity, etc.

Determining Immunogenicity

The purified polypeptide fragments thus obtained can be tested to determine their immunogenicity and specificity. Briefly, various concentrations of a putative immunogenically specific fragment are prepared and administered to an animal and the immunological response (e.g., the production of antibodies or cell mediated immunity) of an animal to each concentration is determined. The amounts of antigen administered depend on the subject, e.g. a human or a guinea pig, the condition of the subject, the size of the subject, etc. Thereafter an animal so inoculated with the antigen can be exposed to the bacterium to test the potential vaccine effect of the specific immunogenic fragment. The specificity of a putative immunogenic fragment can be ascertained by testing sera, other fluids or lymphocytes from the inoculated animal for cross reactivity with other closely related bacteria.

Vectors and Hosts

A vector comprising the nucleic acids of the present invention is also provided. The vectors of the invention can be in a host capable of expressing the antigen.

There are numerous *E. coli* expression vectors known to one of ordinary skill in the art useful for the expression of the antigen. Other microbial hosts suitable for use include bacilli, such as *Bacillus subtilus,* and other Enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of an RNA corresponding to the antigen coding sequence can be confirmed by Northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the DNA segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease NexinI, and eosinophil major basic protein, can be employed. Further, the vector can include CMV promoter sequences and a polyadenylation signal available for expression of inserted DNAs in mammalian cells (such as COS7).

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Purified Antibodies

A purified monoclonal antibody specifically reactive with the antigen is also provided. The antibodies can be specifically reactive with a unique epitope of the antigen or they can also react with epitopes of other organisms. The term "reactive" means capable of binding or otherwise associating nonrandomly with an antigen. "Specifically reactive" as used herein describes an antibody or other ligand that does not cross react substantially with any antigen other than the one specified, in this case, the tagA antigen. Antibodies can be made as described in the Examples (see also, Harlow and Lane, *Antibodies; A Laboratory Manual,* Cold Spring Harbor Laboratory, Cold Spring Harbor, N.Y., 1988). Briefly purified antigen can be injected into an animal in an amount and in intervals sufficient to elicit an immune response. Antibodies can either be purified directly, or spleen cells can be obtained from the animal. The cells are then fused with an immortal cell line and screened for antibody secretion.

The antibody can be bound to a substrate or labeled with a detectable moiety or both bound and labeled. The detectable moieties contemplated with the composition of the present invention are those listed below in the description of the diagnostic methods, including fluorescent, enzymatic and radioactive markers.

Antigen Bound to Substrate

A purified tagA antigen bound to a substrate and a ligand specifically reactive with the antigen are also contemplated. Such a purified ligand specifically reactive with the antigen can be an antibody. The antibody can be a monoclonal antibody obtained by standard methods and as described herein. The monoclonal antibody can be secreted by a hybridoma cell line specifically produced for that purpose (Harlow and Lane, 1988). Likewise, nonhuman polyclonal antibodies specifically reactive with the antigen are within the scope of the present invention. The polyclonal antibody can also be obtained by the standard immunization and purification protocols (Harlow and Lane, 1988).

Serological Detection (Diagnosis) Methods Detecting Antibody with Antigen

The present invention provides a method of detecting the presence of a H. pylori strain possessing the 120–128 kDa antigen in a subject, comprising the steps of contacting an antibody-containing sample from the subject with a detectable amount of the tagA or tagA antigenic fragment of the present invention and detecting the reaction of the tagA or fragment and the antibody, the reaction indicating the presence of the toxic H. pylori strain or previous infection with the toxic H. pylori strain.

Detecting Antigen with Antibody/Ligand

One example of the method of detecting H. pylori possessing the antigen is performed by contacting a fluid or tissue sample from the subject with an amount of a purified antibody specifically reactive with the antigen, and detecting the reaction of the ligand with the antigen. It is contemplated that the antigen will be on intact cells containing the antigen, or will be fragments of the antigen. As contemplated herein, the antibody includes any ligand which binds the antigen, for example, an intact antibody, a fragment of an antibody or another reagent that has reactivity with the antigen. The fluid sample of this method can comprise any body fluid which would contain the antigen or a cell containing the antigen, such as blood, plasma, serum, saliva and urine. Other possible examples of body fluids include sputum, mucus, gastric juice and the like.

ELISA

Immunoassays such as immunofluorescence assays (IFA), enzyme linked immunosorbent assays (ELISA) and immunoblotting can be readily adapted to accomplish the detection of the antigen. An ELISA method effective for the detection of the antigen can, for example, be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect antibody as well as antigen.

Competitive Inhibition Assay

Another immunologic technique that can be useful in the detection of H. pylori expressing tagA or previous H. pylori infection utilizes monoclonal antibodies (MAbs) for detection of antibodies specifically reactive with tagA antigen. Briefly, sera or other body fluids from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.

Micro-Agglutination Assay

A micro-agglutination test can also be used to detect the presence of the tagA-possessing H. pylori strain in a subject. Briefly, latex beads (or red blood cells) are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or by spectrophotometer. In a modification of the above test, antibodies specifically reactive with the antigen can be bound to the beads and antigen in the tissue or body fluid thereby detected.

Sandwich Assay/Flow Cytometry/Immunoprecipitation

In addition, as in a typical sandwich assay, the antibody can be bound to a substrate and reacted with the antigen. Thereafter, a secondary labeled antibody is bound to epitopes not recognized by the first antibody and the secondary antibody is detected. Since the present invention provides tagA antigen for the detection of toxic H. pylori or previous H. pylori infection other serological methods such as flow cytometry and immunoprecipitation can also be used as detection methods.

In the diagnostic methods taught herein, the antigen can be bound to a substrate and contacted by a fluid sample such as serum, urine, saliva or gastric juice. This sample can be taken directly from the patient or in a partially purified form. In this manner, antibodies specific for the antigen (the primary antibody) will specifically react with the bound antigen. Thereafter, a secondary antibody bound to, or labeled with, a detectable moiety can be added to enhance the detection of the primary antibody. Generally, the secondary antibody or other ligand which is reactive, either specifically with a different epitope of the antigen or nonspecifically with the ligand or reacted antibody, will be selected for its ability to react with multiple sites on the primary antibody. Thus, for example, several molecules of the secondary antibody can react with each primary antibody, making the primary antibody more detectable.

Detectable Moieties

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, 1988).

Detecting Disease

Because the purified tagA antigen provided herein is associated with peptic ulceration, the present invention also provides a method of detecting predisposition to peptic ulceration in a subject. The method can be accomplished according to the methods set forth above for the detection of *H. pylori* expressing the tagA antigen or for the detection of antibodies specific to the tagA antigen or for the detection of specific antibodies to the tagA antigen. The presence of the tagA antigen or tagA specific antibodies indicates a predisposition of the subject to peptic ulceration.

Treatment Methods

Methods of treating peptic ulcers in a subject using the compositions of the present invention are provided. For example, in one such method an amount of ligand specifically reactive with the approximately 120–128 kDa antigen of *H. pylori* sufficient to bind the antigen in the subject and improve the subject's clinical condition is administered to the subject. Such improvement results from the ligand interfering with the antigen's normal function in inducing inflammation and cellular damage. The ligand can be a purified monoclonal antibody specifically reactive with the antigen, a purified polyclonal antibody derived from a nonhuman animal, or other reagent having specific reactivity with the antigen. Additionally, cytotoxic moieties can be conjugated to the ligand/antibody by standard methods. Examples of cytotoxic moieties include ricin A chain, diphtheria toxin and radioactive isotopes.

Another method of treating peptic ulcers in a subject comprises administering to the subject an amount of a ligand/antagonist for a receptor for the 120–128 kDa antigen of *H. pylori* sufficient to react with the receptor and prevent the binding of the 120–128 kDa antigen to the receptor. The result is an improvement in the subject's clinical condition. Alternatively, the treatment method can include administering to the subject an amount of an analogue of a tagA receptor to result in competitive binding of the tagA antigen, thus inhibiting binding of the tagA antigen to its wild type receptor. The receptor is localized on cells present in the gastroduodenal mucosa, such as epithelial cells, inflammatory cells, or endothelial cells.

Mutant Organism

The present invention also provides a mutant *H. pylori* in which the tagA gene product has been rendered nonfunctional. In one example, the mutant *H. pylori* strain is obtained by making a substitution mutation in the coding sequence for the tagA antigen as described in the Examples. Since the present invention provides the nucleic acid encoding the antigen, other methods of mutating the coding sequence of the antigen can be used to obtain other mutant strains as contemplated herein. An example of the mutant *H. pylori* strain of the present invention is designated 84–183:M22 and is deposited with the American Type Culture Collection (1230 Parklawn Drive, Rockville, Md. 20852) under ATCC Accession Number 55359.

Additional isogenic mutants can be prepared, for example, by inserting a nucleic acid in the tagA gene or deleting a portion of the tagA gene so as to render the gene non-functional or produced in such low amounts that the organism is non-infectious. Furthermore, by providing the nucleotide sequence for the nucleic acid encoding the antigen, the present invention permits the making of specific point mutations having the desired effect. The deletion, insertion or substitution mutations can be made in the gene sequence in either the regulatory or coding region to prevent transcription or to render the transcribed product nonfunctional.

One such approach to the construction of a deletion or insertion mutant is via the Donnenberg method (Donnenberg and Kaper *Infect. Immun.* 4310–4317, 1991). A deletion in tagA is created by deleting a 0.2 kb BamH1-NdeI fragment and religating the tagA clone. This mutant is cloned into suicide vector pILL570. The sacB gene of *Bacillus subtilis* is also cloned into the suicide vector to provide a conditionally lethal phenotype. This construct is transformed into *H. pylori* by electroporation, and transformants selected by spectinomycin resistance. The merodiploid strain which contains the suicide vector and the mutated version of the tagA gene are exposed to sucrose to directly select for organisms that have undergone a second recombination, resulting in the loss of the vector. These and other well known methods of making mutations can be applied to the nucleic acids provided herein to obtain other desired mutations.

Vaccines

The antigen or mutant *H. pylori* of this invention can be used in the construction of a vaccine comprising an immunogenic amount of the antigen or mutant *H. pylori* and a pharmaceutically acceptable carrier. The vaccine can be the entire antigen, the antigen on an intact *H. pylori*, *E. coli* or other strain. The vaccine can then be used in a method of preventing peptic ulceration or other complications of *H. pylori* infection (including atrophic gastritis and malignant neoplasms of the stomach).

Immunogenic amounts of the antigen can be determined using standard procedures. Briefly, various concentrations of a putative specific immunoreactive epitope are prepared, administered to an animal and the immunological response (e.g., the production of antibodies) of an animal to each concentration is determined.

The pharmaceutically acceptable carrier in the vaccine of the instant invention can comprise saline or other suitable carriers (Arnon, R. (Ed.) *Synthetic Vaccines* I:83–92, CRC Press, Inc., Boca Raton, Fla., 1987). An adjuvant can also be a part of the carrier of the vaccine, in which case it can be selected by standard criteria based on the antigen used, the mode of administration and the subject (Arnon, R. (Ed.), 1987). Methods of administration can be by oral or sublingual means, or by injection, depending on the particular vaccine used and the subject to whom it is administered.

It can be appreciated from the above that the vaccine can be used as a prophylactic or a therapeutic modality. Thus, the invention provides methods of preventing or treating *H. pylori* infection and the associated diseases by administering the vaccine to a subject.

Nucleic Acid Detection (Diagnosis) Methods

The presence of the tagA antigen and *H. pylori* possessing the tagA antigen can also be determined by detecting the presence of a nucleic acid specific for the antigen. The specificity of these sequences for the antigen can be determined by conducting a computerized comparison with known sequences, catalogued in GenBank, a computerized database, using the computer programs Word Search or FASTA of the Genetics Computer Group (Madison, Wis.), which search the catalogued nucleotide sequences for similarities to the gene in question.

The nucleic acid specific for the antigen can be detected utilizing a nucleic acid amplification technique, such as polymerase chain reaction or ligase chain reaction. Alternatively, the nucleic acid is detected utilizing direct hybridization or by utilizing a restriction fragment length polymorphism. For example, the present invention provides a method of detecting the presence of *H. pylori*, possessing the tagA antigen, comprising ascertaining the presence of a nucleotide sequence associated with a restriction endonuclease cleavage site. In addition, PCR primers which hybridize only with nucleic acids specific for the antigen can be utilized. The presence of amplification indicates the presence of the antigen. In another embodiment a restriction fragment of a DNA sample can be sequenced directly using, for example, Sanger ddNTp sequencing or 7-deaza-2'-deoxyguanosine 5'-triphosphate and Taq polymerase and compared to the known unique sequence to detect *H. pylori*. In a further embodiment, the present invention provides a method of detecting the presence of tagA-containing *H. pylori* by selective amplification by the methods described above. In yet another embodiment *H. pylori* can be detected by directly hybridizing the unique sequence with a tagA selective nucleic acid probe. Furthermore, the nucleotide sequence could be amplified prior to hybridization by the methods described above.

Once specific variable sequences are shown to be associated with peptic ulceration, the methods to detect these sequences are standard in the art. Detection of point mutations or variable sequences using direct probing involves the use of oligonucleotide probes which may be prepared, for example, synthetically or by nick translation. The probes may be suitably labeled using, for example, a radio label, enzyme label, fluorescent label, biotin-avidin label and the like for subsequent visualization in the example of Southern blot hybridization procedure. The labeled probe is reacted with a bound sample DNA, e.g., to a nitrocellulose sheet under conditions such that only fully complementary sequences hybridize. The areas that carry DNA sequences complementary to the labeled DNA probe become labeled themselves as a consequence of the reannealing reaction. The areas of the filter that exhibit such labeling may then be visualized, for example, by autoradiography. The labeled probe is reacted with a DNA sample bound to, for example, nitrocellulose under conditions such that only fully complementary sequences will hybridize. The stringency of hybridization is usually 5° C. below the Ti (the irreversible melting temperature of the hybrid formed between the probe and its target sequence) for the given chain length. For 20 mers the recommended hybridization temperature is about 58° C. The washing temperatures are unique to the sequence under investigation and need to be optimized for each variant.

Alternative probing techniques, such as ligase chain reaction (LCR), involve the use of mismatch probes, i.e., probes which are fully complementary with the target except at the point of the mutation. The target sequence is then allowed to hybridize both with oligonucleotides which are fully complementary and have oligonucleotides containing a mismatch, under conditions which will distinguish between the two. By manipulating the reaction conditions, it is possible to obtain hybridization only where there is full complementarity. If a mismatch is present there is significantly reduced hybridization.

The polymerase chain reaction (PCR) is a technique that amplifies specific DNA sequences with remarkable efficiency. Repeated cycles of denaturation, primer annealing and extension carried out with polymerase, e.g., a heat stable enzyme Taq polymerase, leads to exponential increases in the concentration of desired DNA sequences. Given a knowledge of the nucleotide sequence of a mutation, synthetic oligonucleotides can be prepared which are complementary to sequences which flank the DNA of interest. Each oligonucleotide is complementary to one of the two strands. The DNA can be denatured at high temperatures (e.g., 95° C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million-fold can be achieved. The resulting DNA may then be directly sequenced in order to locate any genetic alteration. Alternatively, it may be possible to prepare oligonucleotides that will only bind to altered DNA, so that PCR will only result in multiplication of the DNA if a mutation is present. Following PCR, direct visualization or allele-specific oligonucleotide hybridization may be used to detect disease associated with a point mutation. Alternatively, an adaptation of PCR called amplification of specific alleles (PASA) can be employed; this uses differential amplification for rapid and reliable distinction between alleles that differ at a single base pair. Other techniques, such as 3SR, which utilize RNA polymerase to achieve high copy number, can also be used where appropriate.

In yet another method, PCR may be followed by restriction endonuclease digestion with subsequent analysis of the resultant products. Nucleotide substitutions can result in the gain or loss of specific restriction endonuclease site. The gain or loss of a restriction endonuclease recognition site facilitates the detection of the disease associated mutation using restriction fragment length polymorphism (RFLP) analysis or by detection of the presence or absence of a polymorphic restriction endonuclease site in a PCR product that spans the sequence of interest.

For RFLP analysis, DNA is obtained, for example from the blood, gastric specimen, saliva, dental plaque, other bodily fluids or stool of the subject suspected of containing tagA-possessing *H. pylori*, or *H. pylori* isolated from subject, and from a subject infected with nontoxic *H. pylori*, is digested with a restriction endonuclease, and subsequently separated on the basis of size by agarose gel electrophoresis. The Southern blot technique can then be used to detect, by hybridization with labeled probes, the products of endonuclease digestion. The patterns obtained from the Southern blot can then be compared. Using such an approach, tagA DNA is detected by determining the number of bands detected and comparing this number to the DNA from H. pylori strains that are not associated with severe disease. Restriction endonucleases can also be utilized effectively to detect mutations in the tagA gene.

Similar creation of additional restriction sites by nucleotide substitutions at the disclosed mutation sites can be readily calculated by reference to the genetic code and a list of nucleotide sequences recognized by restriction endonucleases.

Single strand conformational analysis (SSCA) offers a relatively quick method of detecting sequence changes which may be appropriate in at least some instances.

In general, primers for PCR and LCR are usually about 20 bp in length and the preferable range is from 15-25 bp. Better amplification is obtained when both primers are the same length and with roughly the same nucleotide composition. Denaturation of strands usually takes place at 94° C. and extension from the primers is usually at 72° C. The annealing temperature varies according to the sequence under investigation. Examples of reaction times are: 20 mins denaturing; 35 cycles of 2 min, 1 min, 1 min for annealing, extension and denaturation; and finally a 5 min extension step.

PCR amplification of specific alleles (PASA) is a rapid method of detecting single-base mutations or polymorphisms. PASA (also known as allele specific amplification) involves amplification with two oligonucleotide primers such that one is allele-specific. The desired allele is efficiently amplified, while the other allele(s) is poorly amplified because it mismatches with a base at or near the 3' end of the allele-specific primer. Thus, PASA or the related method of PAMSA may be used to specifically amplify the mutation sequences of the invention. Where such amplification is done on $H.$ $pylori$ isolates or samples obtained from an individual, it can serve as a method of detecting the presence of the mutations.

As mentioned above, a method known as ligase chain reaction (LCR) can be used to successfully detect a single-base substitution. LCR probes may be combined or multiplexed for simultaneously screening for multiple different mutations. Thus, LCR can be particularly useful where, as here, multiple mutations are predictive of the same disease.

Antigen-Detecting Kit

The present invention provides a kit for the diagnosis of infection by strains of $H.$ $pylori$ possessing the tagA antigen. Particularly, the kit can detect the presence of tagA antigen specifically reactive with an antibody or an immunoreactive fragment thereof. The kit can include an antibody bound to a substrate, a secondary antibody reactive with the antigen and a reagent for detecting a reaction of the secondary antibody with the antigen. Such a kit can be an ELISA kit and can comprise the substrate, primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

Antibody-Detecting Kit

The diagnostic kit of the present invention can be used to detect the presence of a primary antibody specifically reactive with tagA or an antigenic fragment thereof. The kit can include the antigen bound to a substrate, a secondary antibody reactive with the antibody specifically reactive with the tagA antigen and a reagent for detecting a reaction of the secondary antibody with the primary antibody. Such a kit can be an ELISA kit and can comprise the substrate, antigen, primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

Nucleic Acid Detection (Diagnostic) Kits

Once the nucleotide sequence of the tagA antigen is determined, the diagnostic kit of the present invention can alternatively be constructed to detect nucleotide sequences specific for the antigen comprising the standard kit components such as the substrate and reagents for the detection of nucleic acids. Because $H.$ $pylori$ infection can be diagnosed by detecting nucleic acids specific for the antigen in gastric or duodenal tissue and body fluids such as gastric juice, urine, stool, and saliva, it will be apparent to an artisan that a kit can be constructed that utilizes the nucleic acid detection methods, such as specific nucleic acid probes, primers or restriction fragment length polymorphisms in analyses. It is contemplated that the diagnostic kits will further comprise a positive and negative control test.

The particular reagents and other components included in the diagnostic kits of the present invention can be selected from those available in the art in accord with the specific diagnostic method practiced in the kit. Such kits can be used to detect the antigen in tissue and fluid samples from a subject.

The following examples are intended to illustrate, but not limit, the invention. While they are typical of those that might be used, other procedures known to those skilled in the art may be alternatively employed.

EXAMPLE 1

Cloning and Expression of tagA Antigen

Bacterial strains and growth conditions.

$H.$ $pylori$ strain 84–183 (ATCC 53726) was used to clone the gene for the tagA antigen. Thirty-two clinical $H.$ $pylori$ isolates from humans, including strains that had been previously shown to possess the antigen, were used to assess conservation of the gene and correlation with cytotoxin production (Table 1). Stock cultures were maintained at −70° C. in Brucella broth (BBL Microbiology Systems, Cockeysville, Md.) supplemented with 15% glycerol. $H.$ $pylori$ strains were cultured in Brucella broth supplemented with 5% fetal bovine serum in a microaerobic atmosphere (generated by CampyPak-Plus (BBL) at 37° C. for 48 hours. For transformation and protein expression, $E.$ $coli$ strains XL1-Blue (Stratagene, La Jolla, Calif.), HB101 (ATCC 33694), and DH5α (Stratagene, La Jolla, Calif.) were cultured in Luria-Bertoli (LB) medium with shaking at 37° C. The final concentrations of ampicillin when added to media was 100 μg/ml.

Chemicals and enzymes.

Isopropyl-β-D-thiogalactopyranoside (IPTG) was purchased from Sigma Chemical Co. (St. Louis, Mo.) and used at 57 μg/ml, and 5-bromo-4-chloro-3-indolyl-β-D-galactoside (X-GAL; final concentration 40 μg/ml) was from Boehringer-Mannheim (Indianapolis, Ind.). Restriction enzymes, T4 DNA ligase, $E.$ $coli$ DNA polymerase large (Klenow) fragment and Sequenase ™ were from Promega and United States Biochemicals (Cleveland, Ohio). [α-$^{32}$P] dATP (650

Ci/mmol) was from ICN Radiochemicals (Irvine, Calif.).

Genetic techniques and nucleotide sequence analysis.

To obtain chromosomal DNA from *H. pylori* 84-183, the strain was cultured for 48 h in Brucella broth containing 5% fetal bovine serum, the cells pelleted, and resuspended in 100 mM Tris-HCl (pH 7.2) containing 100 mM NaCl. Cells were lysed using 1% SDS in 100 mM Tris-HCl (pH 8.8). After chloroform-phenol extractions, the chromosomal DNA was precipitated with 100% ethanol. Plasmids were isolated by the rapid alkaline extraction procedure of Birnboim and Doly (*Nucleic Acids. Res.*, 7:1513-1523, 1979) and purification was completed by precipitation in the presence of 800 mM NaCl and 6.5% polyethylene glycol. All other standard molecular genetic techniques, including sequential ordered deletions, were performed as described (Sambrook et al. *Molecular cloning: A Laboratory Manual*, 1989). The nucleotide sequence was determined unambiguously on both strands using double-stranded DNA templates and the dideoxy chain termination procedure as described previously (Sanger et al. *Proc. Natl. Acad. Sci. U.S.A.*, 71:1342-1346.32, 1977). Oligonucleotide primers were synthesized by the Vanderbilt University DNA Core Facility using a Milligen 7500 DNA synthesizer, using the manufacturer's protocol. Nucleotide sequences were compiled and analyzed with the aid of the DNA-Star program (DNA Star, Inc., Madison, Wis.); putative promoter and Shine-Dalgarno sequences were identified by comparison with consensus sequences (Hawley and McClure *Nucleic Acids Res.* 11:2237-2255, 1983).

Construction of a genomic library from *H. pylori*.

Strain 84-183 chromosomal DNA was sheared by sonication and the resulting fragments were electrophoresed on a 0.7% low melting temperature agarose gel. Fragments in the 2-10 kb size range were excised, treated with T4 DNA polymerase to produce blunt ends, and ligated to phosphorylated EcORI octamer linkers (New England Biolabs, Beverly, Mass.). The DNA was digested with EcoRI and ligated to the EcoRI arms of the λZapII vector, according to the manufacturer's protocol. The ligation mixtures were added to the Gigapack IIa packaging mix (Stratagene) and titered on XL1-blue cells (lambda ZapII) or Y1088 (lambda gt11) cells. The amplified phage libraries were screened with adsorbed sera from an *H. pylori*-infected person or by plaque hybridization.

Cloning of *H. pylori*-specific genes.

Serum from an *H. pylori*-infected person that strongly recognizes the 120-128 kDa antigen was adsorbed with *H. pylori* strain 86-313, which does not produce the 120-128 kDa band, and with *E. coli* cells to reduce the likelihood of nonspecific reactivity and then used to screen a bank of genes from the amplified λZapII phage library (Blaser and Gotschlich *J. Biol. Chem.* 265:14529-4535, 1990). The bank contained approximately $4 \times 10^4$ insertions. The amplified phage library was screened by allowing approximately $10^5$ plaques to grow on XL1 Blue cells for 2.5 h at 42° C., overlaying with a nitrocellulose filter previously impregnated with 10 mM IPTG, and incubating for 2 h at 37° C. The filters were then screened with the adsorbed serum to detect 9 reactive clones. Positive plaques were then plaque purified, and lysates were prepared from these infected *E. coli* cells. The lysates were immunoblotted with the adsorbed serum and clones expressing recombinant proteins were saved. By immunoblotting with the adsorbed human serum, each of the XL1-Blue lysates showed a strongly immunoreactive band migrating at either approximately 75, 85, or 96 kDa, corresponding to plasmids pMC1, pMC2, or pMC3, respectively.

From the three representative clones, the pBluescript plasmids containing the cloned DNA inserts were excised by co-infection with helper phage, as detailed (Short et al. *Nucleic Acids Res.*, 16:7583-7600, 1988), and fresh XL1-Blue cells transformed. After plasmid purification, restriction enzyme cleavage maps were generated and the plasmids used for further characterization. In a parallel study, four clones were isolated from a λgt11 library of *H. pylori* 84-183 DNA by the same methodology, and the DNA insert from one of four positive clones was amplified by polymerase chain reaction (PCR) using primers based on the known flanking λgt11 sequences. Recombinant phage DNA from four positive plaques was purified, and each contained a 0.6 kb insert. Immunoblot analysis of lysates from two clones (λYB1 and λYB2) showed similar sized 130 kDa bands that reacted with the adsorbed human antiserum. To determine whether the 130 kDa protein was synthesized by a recombinant phage as a fusion protein, cell lysate prepared from λYB1 was subjected to immunoblot analysis using β-galactosidase specific antiserum. The cross-reactivity shown indicates that the recombinant clone λYB1 contains a fusion of the λkgt11 β-galactosidase large (116 kDa) fragment and an *H. pylori* open reading frame. We cloned the λYB1 insert into pUC19, but the recombinant (pYB1) did not express any protein.

Gel electrophoresis and immunoblot analysis.

Lysates from *E. coli* carrying recombinant lambda gt11, λZapII or pBluescript were analyzed by SDS-PAGE and immunoblotting with adsorbed human serum. Discontinuous sodium dodecyl sulfate (SDS)-poly-acrylamide gel electrophoresis (PAGE) was performed as described previously (Blaser et al. *Infect. Immun.*, 42:276-284, 1983) by using a 4.5% stacking gel and a 7.0% separating gel. Samples containing 3 µg of protein were applied to each gel lane. After electrophoresis, gels were fixed and proteins were resolved by the modified silver stain method of Oakley et al. (*Anal. Biochem.* 105:361-363, 1980). Concentrated culture supernatants containing protein were diluted in sample buffer and were layered onto the surface of a polyacrylamide gel in a Mini-PROTEAN II slab cell (Bio-Rad Laboratories, Richmond, Calif.). Following electrophoresis, proteins were transferred to nitrocellulose paper by electro blotting for 1 h at 1 amp. After nonspecific binding was blocked, the nitrocellulose paper was incubated at room temperature for 1 h with 1:100 dilutions of serum samples. Alkaline-phosphatase conjugates of goat anti-human IgG, (Tago, Inc., Burlingame, Calif.), in a dilution of 1:2,000 were used as the second antibody.

Southern hybridization.

*H. pylori* or *C. jejuni* chromosomal DNA was digested with either HindIII or EcoRI and BamHI and the resulting fragments were electrophoresed on a 0.7% agarose gel in 0.04M Tris-acetate −2 mM EDTA buffer (pH 8.2). All hybridization conditions and procedures were exactly as described (Sambrook et al, 1989). Probes were radiolabeled by primer extension using random hexamers (Feinberg and Bogelstein *Anal. Biochem*, 132:6-13, 1983). Hybridization was carried out at 68° C. for 16h in buffer containing 6X SSC (1X SSC is 0.15M NaCl, 0.015M sodium citrate), 0.5% sodium dodecyl sulfate (SDS), 5X Denhardt's solution (1X Denhardt's solution is 0.02% Ficoll, 0.02% polyvinylpyrrolidone, 0.02% bovine serum albumin), and 100 μg/ml salmon sperm DNA. The blots were washed at 60° C. in 0.5X SSC and exposed to XAR-2 X-ray film (Eastman Kodak, Rochester, N.Y.).

Colony hybridization.

*H. pylori* strains were grown on trypticase soy blood agar plates (BBL) and replica copies of these colonies were transferred to nitrocellulose filters. Each filter was placed on 3 mm Whatman paper saturated with 0.2M NaOH/1.5M NaCl. After 3 min the filter was transferred to 3 mm Whatman paper saturated with 0.4M Tris-Cl (pH 7.6)/2X SSC for 3 min, and then to 2X SSC for 3 min. The colony blot filters were dried in a vacuum oven for 90 min at 80° C. and hybridized with radiolabeled pMC3 as described (Sambrook et al, 1989).

Cytotoxin production.

*H. pylori* broth culture supernatants were concentrated 30-fold by ultrafiltration, passaged through a 0.2 μM filter, and incubated with HeLa cells. Briefly, *H. pylori* strains were cultured at 37° C. in brucella broth (BBL, Microbiology Systems, Cockeysville, Md.) containing 5% defined fetal bovine serum (Hyclone, Logan, Utah), supplemented with 10 mM ammonium chloride to potentiate cytotoxin activity. Broth cultures were incubated in a microaerobic atmosphere on a gyratory shaker at 100 rpm for 72 h. Cultures were centrifuged at 3,000×g for 15 min, and the cell-free supernatants were stored at −70° C. After thawing, supernatants were concentrated 30-fold by using a 30-kDa ultrafiltration membrane, and retentates were sterilized by passage through a 0.22-μm-pore-size filter. These concentrated culture supernatants ($CCS_s$) were incubated with HeLa cells (obtained from Allison O'Brien, Uniformed Services University of the Health Sciences, Bethesda, Md.) in twofold dilutions from 1:10 to 1:320 as described previously (Leunk et al. *J. Med. Microbiol.* 26:93–99, 1988), except that toxicity assays were performed in a total volume of 100 μl in 96-well microtiter plates (Falcon; Becton Dickinson and Co., Lincoln Park, N.J.).

Vacuolation of HeLa cells was quantitated using a neutral red uptake assay. Briefly, a stock solution of 0.5% purified grade neutral red (Sigma Chemical Co., St. Louis, Mo.) was prepared in 0.9% saline and filtered with Whatman no. 1 filter pater. Staining solutions were prepared before each experiment by diluting the stock solution 1:10 in Eagle medium containing 10% fetal bovine serum. After incubation with test samples for 24 h the medium overlaying HeLa cells was removed and replaced with 100 μl of staining solution per well for 4 min. The cells were washed twice with 150 μl of 0.9% saline per well, and the neutral red was extracted from cells by the addition of 100 μl of acidified alcohol per well (Montefiori et al. *J. Clin. Microbiol.* 26:231–235, 1988). The optical density (OD) at 540 nm of wells was determined by using an MR700 enzyme-linked immunosorbent assay reader (Dynatech, Alexandria, Va.). All assays were performed in triplicate. In all experiments, the mean OD of wells containing cells incubated with medium alone was less than 0.130 (mean, 0.101±0.007); this background OD was subtracted from the OD of experimental wells to yield a net OD. Of the 32 *H. pylori* strains tested, 15 produced the vacuolating cytotoxin, as determined in this assay (Table 3).

Mapping the pBluescript inserts.

After digestion with EcoRI, plasmids pMC1, pMC2, and pMC3 were found to contain DNA inserts of approximately 2.5, 2.7, and 3.6 kb, respectively. Analysis of restriction endonuclease treatment of the recombinant plasmids identified a conserved 1.2 kb HindIII-digestion fragment in all three (FIG. 1). As such, further studies concentrated on pMC3, which contained the largest insert. Analysis of deletion mutations produced by exonuclease III digestion, identified the orientation and approximate location of the open reading frame (ORF) (FIG. 1, large arrow).

Sequence analysis of pMC3 and pYB1.

To determine the sequence of the 3.6 kb insert in pMC3, a series of nested ordered deletions of the plasmid using exonuclease III (FIG. 1) was performed, as described (Sambrook et al., 1989). In total, the sequence for the entire pMC3 insert representing 3648 bp was determined on both strands (SEQ ID NO:1). The nucleotides are numbered on the right of each line. The nucleotides encoding the glycine at residue number 859 of SEQ ID NO:1 are an artifact of the cloning process and are not a part of the tagA gene. SEQ ID NO:2 provides the deduced amino acid sequence of the nucleic acid shown in SEQ ID NO:1.

A long open reading frame commencing at nucleotide 1072 continues to the termination of the insert. Two other open reading frames in the opposite orientation begin at 645 bp and 264 bp. The deduced amino acids are shown beneath the nucleotides. Potential ribosomal binding-sites (Shine-Delgarno sequence; SD), and putative promoter elements (−35 and −10 sequences) are indicated. Only a single ORF exceeding 300 bases was found in any of the six possible reading frames. This ORF encodes a tagA antigen of 859 amino acids, yielding a predicted protein with a molecular weight of 96,022 (SEQ ID NO: 2). The direction of transcription deduced from this ORF is also in agreement with that determined previously by the use of the deletion mutants. However, there is no translation termination signal, indicating that the ORF in pMC3 is truncated. The truncated fragment is rich in basic amino acids (Table 2) and the predicted isoelectric point is 8.0. A potential ribosomal binding site (AGGAG) ends 6 bp upstream of the ORF. The sequence 112 bp upstream of the translational start site exhibits the promoter sequence TATAGT (SEQ ID NO: 1) which resembles the Pribnow consensus promoter sequence TATNATN (Hawley and McClure). This putative −10 region, which is similar to a sigma-70 promoter, is associated with a −35 region, ATGCCA, which shares 4 of 6 bases with the corresponding consensus sequence, TTGACA (Hawley and McClure, 1983). The deduced amino acid composition of the truncated polypeptide is shown in Table 2.

Two smaller ORFs, each proceeding in the opposite direction, also were identified (SEQ ID NO: 1). The first, encoding a polypeptide of 79 amino acids, commences at bp 645 and is not proceeded by an obvious Shine Delgarno or putative promoter sequence. The second ORF commences at bp 264 and encodes 88 amino acids before the end of the insert. This truncated ORF is preceded by a Shine Dalgarno sequence, and the sequence TTTGAT 90 bp upstream of the translational start site resembles the −10 consensus promoter site, followed by the sequence TTGTCA, which shares 5 of 6 bases with the −35 consensus sequence (Hawley and McClure, 1983).

The 0.6 kb insert in pYB1 was sequenced using both forward and reverse primers of the known λgt11 flanking sequences along with additional primers based on experimentally-derived insert sequences. The first 464 bases of the 620 bp pYB1 sequence overlapped with the 5 end of pMC3, but the ORF still continued.

Serologic recognition of the truncated recombinant tagA antigen.

In addition to the index case, sera from *H. pylori*-infected persons that recognize the tagA antigen from *H. pylori* strain 84–183 recognize the recombinant polypeptide. For this analysis, we studied serum from 6 persons not infected with *H. pylori*, and from 14 infected persons (7 did and 7 did not recognize the 120–128 kDa antigen from strain 84–183). Using lysates of *E. coli* XL1-Blue transformed with pMC3 and immunoblotting, there is clear recognition of the 96 kDa antigen by human serum IgG. In total, 4 of 7 sera that recognize the native 120–128 kDa band also strongly recognize the recombinant protein versus none of the 13 sera tested that do not recognize the 120–128 kDa band (p=0.007, Fisher's exact test, 2-tailed). If weak reactions to the pMC3 band are considered, then all 7 sera that recognize the 120–128 kDa band, and 3 of 13 of the non-recognizing sera react to the recombinant protein (p=0.003, Fisher's exact test, 2-tailed). Thus, the recombinant protein produced by pMC3 can be used for serologic assays to detect antibodies to the *H. pylori* 120–128 kDa antigen.

Conservation of the tagA gene.

To determine whether other *H. pylori* strains possess the tagA gene or homologous sequences, 32 strains were studied by colony hybridization using pMC3 as a probe (Table 3). A positive signal was obtained from 19 (59.3%) of these strains. SDS-PAGE and immunoblotting of whole cells of these strains indicated that 19 (59.3%) of the 32 strains expressed a band at 120–128 kDa. The immunoblot and colony hybridization findings correlated completely; all 19 *H. pylori* strains expressing the protein possessed a gene homolog, in comparison to none of the 13 strains not expressing the protein (p<0.001, Fisher's exact test, one-tailed). In addition, all 15 strains producing the vacuolating cytotoxin showed both pMC3 hybridization and presence of the 120–128 kDa band (Table 3).

To gain information on the restriction fragment polymorphism of the tagA gene and whether there are multiple homologous genes in each bacterial genome, genomic DNA from 4 *H. pylori* strains was prepared and Southern hybridization performed using pMC3 as the probe. Two strains expressing the 120–128 kDa protein and with positive colony hybridization now showed strong hybridization to a HindIII restriction fragment migrating at approximately 1.2 kb, and weaker bands at 3.0 and 3.3 kb. For a third strain that showed the phenotype and had a positive colony hybridization, the probe hybridized strongly in the Southern analysis to a band of about 1.1 kb; no weaker bands were seen. A band migrating at less than 0.5 kb that hybridized weakly with the probe was present in all three strains. An *H. pylori* strain that expressed no 120–128 kDa protein and that had a negative colony hybridization, as well as a *C. jejuni* strain used as a control, showed lack of hybridization in the Southern analysis. Hybridization of pMC3 to chromosomal DNA from strains 84–183 and 60190 digested with EcoRI and BamHI also showed polymorphism, confirming the heterogeneity observed with the other restriction enzyme. These studies indicate that although homologs of tagA exist in other *H. pylori* strains, there is heterogeneity in either intragenic or flanking sequences.

The present example provides a cloned fragment of *H. pylori* genomic DNA that includes the majority of a gene that encodes an important *H. pylori* antigen. The evidence that pMC3 contains the gene encoding the tagA antigen may be summarized as follows: (i) neither the protein nor the gene are present in all *H. pylori* strains; (ii) only strains expressing the 120–128 kDa protein hybridize with pMC3 and strains that do not express the protein do not hybridize; (iii) sera from *H. pylori*-infected persons that recognize the 120–128 kDa antigen recognize the recombinant tagA product significantly more frequently than do control sera.

The partial sequences of tagA and the two other ORFs have no identity with the N-terminus or 3 internal sequences from the 87 kDa cytotoxin. This finding is consistent with earlier observations that the 120–128 kDa and 87 kDa proteins are antigenically unrelated (Cover and Blaser *J. Biol. Chem.*, 1992). Comparison of the truncated deduced gene product revealed little direct homology with known proteins.

The tagA gene or homologous genes are present in approximately 60% of the *H. pylori* isolates studied but absent from the others. As indicated by the Southern analysis, there is evidence for restriction fragment polymorphism even when only a small number of strains are examined. Absence of a homolog correlated exactly with lack of expression of an antigenic band at 120–128 kDa. Thus, the phenotype lacking this band is not due to deficiencies related to transcription or expression but rather to the absence of the implicated gene.

The presence of genomic DNA containing at least the truncated tagA gene is highly associated with cytotoxin production. A minority of strains that possess the tagA gene do not produce detectable levels of cytotoxin. This phenomenon may reflect suboptimal sensitivity in the cell culture assay to detect toxin, or may indicate that factors other than the tagA antigen are associated with toxin activity.

As shown by the immunoblot studies, the pMC3 products are excellent diagnostic reagents for detection of human serum antibodies to the tagA antigen. Use of this recombinant protein can readily supply sufficient antigen to aid in development of immunoassays to determine which persons are infected with *H. pylori* strains producing the native 120–128 kDa protein, and heterologous antibodies raised against the pMC3 gene product can be used to determine which strains produce the tagA antigen. Knowledge of the DNA sequence of pMC3 permits the construction of oligonucleotides for use as hybridization probes or for primers for PCR. Such techniques are also used for rapid detection of infection due to a strain with the implicated genotype. Creation of deletion mutants enables elucidation of the role of this gene product and provides both therapeutic reagents and vaccine candidates. Such diagnostic methods and mutants are detailed herein.

TABLE 1

| Helicobacter pylori strains used in this study | | |
|---|---|---|
| Strain designation | Isolation locale | Expression of 120–128 kDa antigen[a] | Expression of vacuolating cytotoxin activity[b] |
| Tx3Oa | Texas | − | − |
| 84-183 | Texas | + | + |
| 60190 | England | + | + |
| 87-29 | Colorado | + | + |

TABLE 1-continued

Helicobacter pylori strains used in this study

| Strain designation | Isolation locale | Expression of 120–128 kDa antigen[a] | Expression of vacuolating cytotoxin activity[b] |
|---|---|---|---|
| 86-313 | Colorado | − | − |
| 87-199 | Colorado | + | + |
| 86-385 | Colorado | − | − |
| 87-33 | Colorado | + | + |
| 87-81 | Colorado | + | + |
| 87-91 | Colorado | + | + |
| 87-90 | Colorado | − | − |
| 87-226 | Colorado | + | − |
| 87-225 | Colorado | − | − |
| 87-230 | Colorado | − | − |
| 87-75 | Colorado | − | − |
| 87-203 | Colorado | − | − |
| 87-6 | Colorado | + | − |
| 86-338 | Colorado | − | − |
| 86-63 | New York | + | − |
| 86-86 | New York | + | + |
| 86-332 | Minnesota | + | + |
| 92-18 | Tennessee | + | + |
| 92-19 | Tennessee | + | + |
| 92-20 | Tennessee | − | − |
| 92-21 | Tennessee | + | + |
| 92-22 | Tennessee | + | − |
| 92-23 | Tennessee | − | − |
| 92-24 | Tennessee | − | − |
| 92-25 | Tennessee | + | + |
| 92-26 | Tennessee | + | + |
| 92-27 | Tennessee | + | + |
| 92-28 | Tennessee | − | − |

[a]Recognition of 120–128 kDa band in cell lysates by human serum as detected by immunoblot (Cover et al., 1990).
[b]Production of vacuolating cytotoxin as detected in HeLa cell culture (Cover et al. Infect. Immun. 59:1264–1270, 1991).

TABLE 2

Amino acid composition of truncated 859 amino acid tagA polypeptide as deduced from pMC3

| Amino acid | Number of residues | Percent of 859 amino acids |
|---|---|---|
| Ala | 60 | 7.0 |
| Cys | 2 | 0.2 |
| Asp | 62 | 7.2 |
| Asn | 82 | 9.5 |
| Glu | 59 | 6.9 |
| Gln | 48 | 5.6 |
| Phe | 44 | 5.1 |
| Gly | 54 | 6.3 |
| His | 12 | 1.4 |
| Ile | 50 | 5.8 |
| Lys | 101 | 11.8 |
| Leu | 67 | 7.8 |
| Met | 12 | 1.4 |
| Pro | 24 | 2.8 |
| Arg | 22 | 2.6 |
| Ser | 63 | 7.3 |
| Thr | 30 | 3.5 |
| Val | 47 | 5.5 |
| Trp | 4 | 0.4 |
| Tyr | 16 | 1.9 |

TABLE 3

Correlation between presence of 120–128 kDa band by immunoblot, hybridization with pMC3, and cytotoxin production by 32 H. pylori isolates from humans

| Presence of 120–128 kDa band on immunoblot[a] | Hybridization of pMC3 to H. pylori colony[b] | Cytotoxin production in cell culture assay[c] | Number of strains |
|---|---|---|---|
| + | + | + | 15 |
| − | − | − | 13 |
| + | + | − | 4 |
| − | − | + | 0 |
| − | + | − | 0 |
| + | − | − | 0 |
| + | − | + | 0 |
| − | + | + | 0 |

[a]Recognition of 120–128 kDa band in cell lysates by human serum as detected by immunoblot (Cover et al., 1990).
[b]Hybridization of pMC3 to lysed H. Pylori cells in colony blot (Sambrook et al., 1989).
[c]Production of vacuolating cytotoxin as detected in HeLa cell culture (Cover et al., 1991).

EXAMPLE 2

Construction and characterization of a tagA-negative strain of *Helicobacter pylori*

Bacterial strains, vectors and growth conditions.

*H. pylori* strain 84–183 (ATCC 53726) used in this study was from the culture collection of the Vanderbilt University Campylobacter/Helicobacter Laboratory and was chosen because it has been extensively characterized. Stock cultures were maintained at −70° C. in Brucella broth (BBL Microbiology Systems, Cockeysville, Md.) supplemented with 15% glycerol. *H. pylori* strains were grown in Brucella broth supplemented with 5% fetal bovine serum or on blood agar plates supplemented with nalidixic acid (50 mg/liter), vancomycin (10 mg/liter), polymyxin B (5000 U/liter), and trimethoprim (5 mg/liter) under microaerobic conditions at 37° C. for 48 hours. *E. coli* strain DH5α (Stratagene, La Jolla, Calif.) used for transformation, was grown in LB medium. As described above, pMC3 contains the truncated tagA gene on a 3.5 kb insert in pBluescript. Plasmid pILL600 (Labigne-Roussel et al. *J. Bacteriol.*, 170:1704, 1988) was used as a source of a *C. coli* kanamycin (km) resistance gene.

Chemicals and enzymes.

Final concentrations of ampicillin (100 μg/ml) and kanamycin (50 μg/ml) were used whenever necessary. Restriction enzymes, T4 DNA ligase, *E. coli* DNA polymerase large (Klenow) fragment were from Promega and United States Biochemicals (Cleveland, Ohio). α-$^{32}$P-dATP (650 Ci/mmol) was from ICN Radiochemicals (Irvine, Calif.).

Genetic techniques.

Chromosomal DNA was prepared as described above. Plasmids were isolated by the procedure of Birnboim and Doly (1979). All other standard molecular genetic techniques were performed as described (Sambrook et al., 1989). DNA fragments used as probes for hybridization experiments were gel-purified.

Introduction of km cassette into *H. pylori* strain 84–183.

Figure 2:
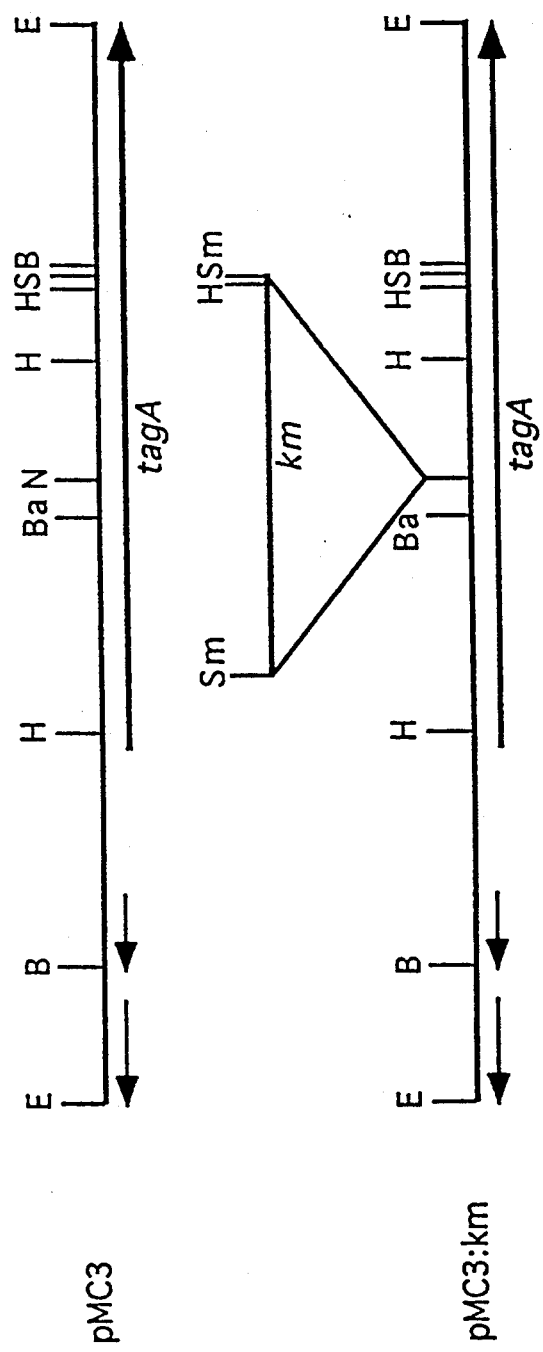
FIG. 2 shows a restriction map of pMC3:km used in construction of *H. pylori* mutant. The km cassette from pILL600 was ligated into the NdeI site of pMC3 to create pMC3:km. The arrows represent open reading frames including the truncated 2577 bp tagA open reading frame. Restriction sites are E, EcoRI; B, BglII; H, HindIII; Ba, BamHI; N, NdeI; S, SacI; Sm, SmaI. pMC4 represents the 2.9 kb EcoRI to SacI fragment of pMC3.

An *E. coli* kanamycin-resistance gene was inserted into the unique NdeI site of pMC3 to create pMC3:km (FIG. 2). This construct was introduced directly into *H. pylori* strain 84–183 by electroporation. Briefly, *H. pylori* cells grown on blood agar plates for 48 h were harvested, washed three times in electroporation buffer (15% glycerol/5% sucrose) and suspended in 200 μl of the buffer. Plasmid DNA from pMC3:km was isolated by a rapid (mini-prep) alkaline-lysis method of Birnboim and Doly and was added to the cells and incubated for 5 min on ice. The cells and DNA were transferred to 0.2 cm electroporation cuvette in a Gene-pulsar apparatus (Bio-Rad), and high voltage pulses (25F, 2.5 kv and 200Ω) were delivered as described previously (Ferrero et al. *J, Bacteriol.,* 174:4212, 1992). Following electroporation, the cells were suspended in 400 μl of LB media and spread on blood agar plates. The plates were incubated at 37° C. under microaerobic conditions for 24 h, then cells were harvested, plated on blood agar plates containing 50 μg/ml of kanamycin, and incubated microaerobically for 48 h.

The cloning vector used was unable to replicate in *H. pylori* and selection on kanamycin-containing media yielded kanamycin-resistant recombinants. From approximately $10^{10}$ *H. pylori* cfu, 3000 transformants $(10^{-7})$ were obtained when 500 ng of plasmid DNA was used.

Colony hybridization.

Fifty kanamycin-resistant transformants obtained by electroporation were grown on blood agar plates and replica copies of these colonies were transferred to nitrocellulose filters. Each filter was placed on 3 mM Whatman paper saturated with 0.2M NaOH/1.5M NaCl. After 3 min the filter was transferred to 3 mM Whatman paper, saturated with 0.4M Tris-HCl (pH 7.6)/2×SSC for 3 min, and then to 2×SSC for 3 min. The colony blot filters were dried in a vacuum oven for 90 min at 80° C. and hybridized with radiolabeled pBluescript or the km-resistance gene, as described above. The colony blots were washed at 60° C. in 0.5X SSC and exposed to XAR-2 X-Ray film (Eastman Kodak, Rochester, N.Y.).

Gel electrophoresis and immunoblot analysis.

Lysates of *E. coli* carrying pBluescript, pMC3 or pMC3:km or of *H. pylori* cells were prepared and analyzed by SDS-polyacrylamide gel electrophoresis (SDS-PAGE). Immunoblotting of whole cell extracts derived from wild-type and mutants 1, 21 and 22 was performed as detailed above using a 1:300 dilution of adsorbed human sera, and a 1:2000 dilution of goat anti-human immunoglobulin alkaline phosphatase conjugate as the secondary antibody, as described above. These studies showed that isogenic mutant strains 1, 21, and 22 have no antigenic tagA gene product.

Southern hybridizations.

Southern hybridization of wild-type *H. pylori* strain 84–183 and kanamycin-resistant transformants M21 and M22 were performed. *H. pylori* chromosomal DNA was digested with HindIII or BamHI and SacI and the resulting fragments were electrophoresed on a 0.7% agarose gel and transferred to nylon membrane. Probes were gel-purified DNA fragments derived from pMC4 or pILL600 and were radiolabeled by primer extension using random hexameric oligonucleotides as described above. The DNA was then transferred to a nylon membrane and hybridized with $^{32}$P-labeled pMC4 or the 1.3 kb km cassette under conditions of high stringency. Hybridizations were performed in a solution of 6X SSC, 0.5% SDS, 5X Denhardt's solution and 100 μg/ml salmon sperm DNA and the blots were washed for 30 min. at 60° C. in 0.5X SSC/0.1% SDS.

Genotypic characterization of the transformants.

To provide genetic evidence that the tagA gene is disrupted in the transformant strains, DNA isolated from wild-type strain 84–183 and *H. pylori* mutants 21 and 22 was digested with the restriction endonuclease HindIII or BamHI and SacI. After separation of the digested DNA on an agarose gel the DNA was transferred to a nylon membrane and hybridized to pMC4 which is a tagA probe. This probe hybridized to approximately 20 and 1.0 kb BamHI-SacI fragments in the wild-type strain, whereas the 1.0 kb BamHI-SacI fragment is lost and a new 2.3 kb hybridizing fragment was observed in both mutant strains without disruption of the other bands. Similarly, a 1.2 kb HindIII fragment was lost and a 2.2 kb fragment gained in both mutants because of the kanamycin resistance gene insertion. The kanamycin gene probe hybridized only with the 2.3 kb BamHI-SacI and 2.2 kb HindIII fragment in mutants 21 and 22 strains, which indicate that replacement had occurred in the tagA gene. Thus, the tagA gene in strain 84–183 had been mutagenized by insertion of the km gene.

Cytotoxin production.

Cytotoxin production was assayed as described above and the results shown in Table 4. The results indicate that neither the intact tagA antigen nor the intact tagA gene is required for vacuolation.

TABLE 4

| Supernatant dilution | Cytotoxin production by wild-type *H. pylori* strains and tagA$^-$ mutants | | | |
|---|---|---|---|---|
| | Optical density$^a$ | | | |
| | 84-183 | M1 | M22 | 87-203$^b$ |
| 1:5 | 0.21 ± 0.04 | 0.26 ± 0.04 | 0.23 ± 0.05 | 0 ± 0.02 |
| 1:10 | 0.16 ± 0.02 | 0.20 ± 0.03 | 0.13 ± 0.02 | 0.01 ± 0.01 |
| 1:20 | 0.13 ± 0.01 | 0.15 ± 0.02 | 0.10 ± 0.02 | 0.01 ± 0.01 |
| 1:40 | 0.09 ± 0.02 | 0.06 ± 0.01 | 0.06 ± 0.02 | 0.01 ± 0 |
| 1:80 | 0.03 ± 0.01 | 0.04 ± 0 | 0.02 ± 0.01 | 0.01 ± 0 |
| 1:160 | −0.01 ± 0.02 | −0.01 ± 0.01 | −0.01 ± 0.02 | −0.02 ± 0.02 |

$^a$Net optical density as measured in neutral red assay of cytotoxin-induced vacuolation, as described above (Cover et al., 1991).
$^b$Strain 87-203 is a strain known not to produce cytotoxin.

EXAMPLE 3

Full Length tagA Gene and Gene Product

Cloning and sequencing of the full length gene.

Figure 3:
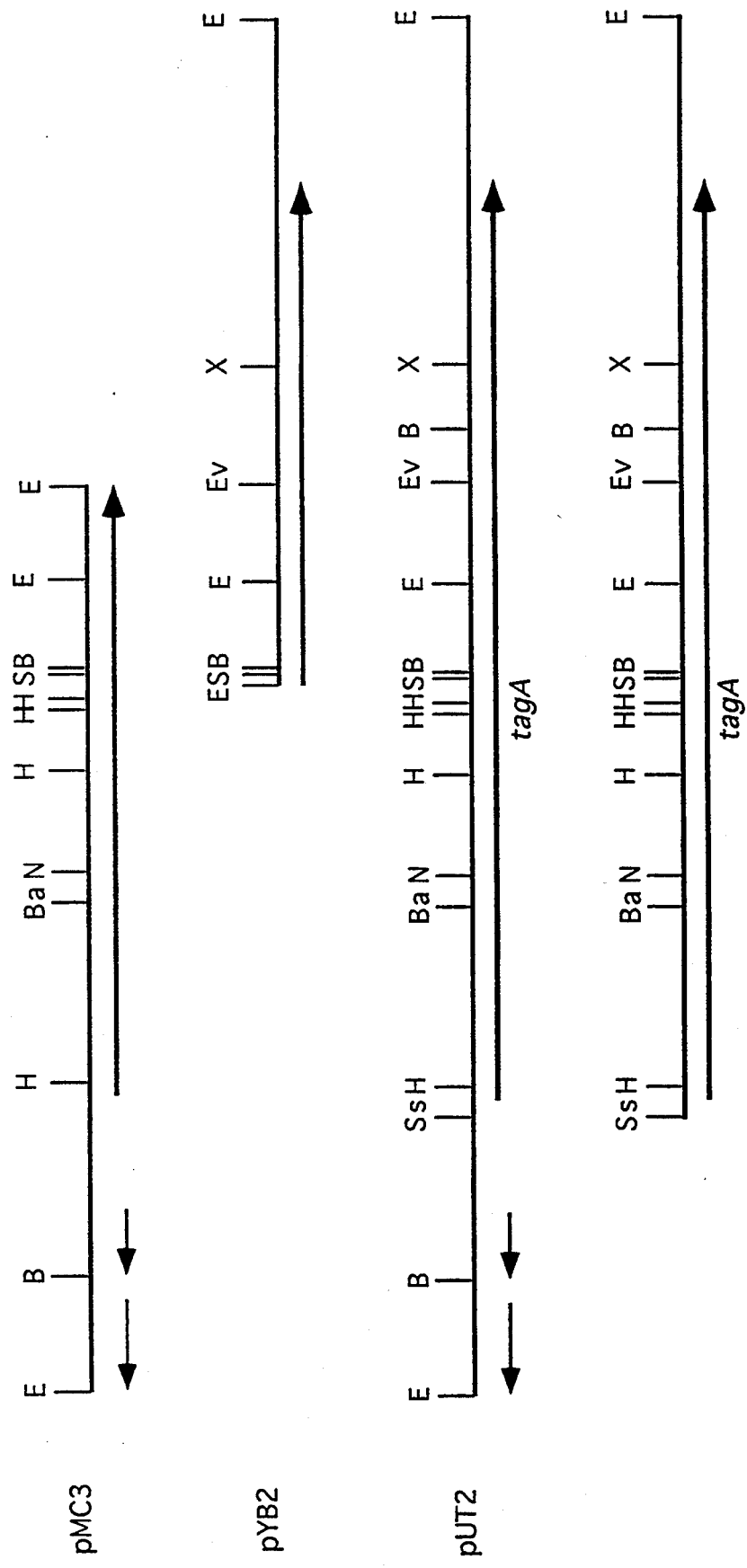
FIG. 3 shows physical maps of plasmids pMC3, pYB2 and pUT2. The large arrow beneath pUT2 represents the location of the tagA gene and the direction of transcription as determined by deletion mutations and immunoblotting. Restriction endonuclease cleavage sites: B, BglII; Ba, BamHI; E, EcoRI; EV, EcoRV; H, HindIII; N, NdeI; S, SacI; X, XbaI.

To isolate the full-length gene, we next used the 0.6 kb fragment of pYB1 as a probe to screen the λZapII library of *H. pylori* 84–183. Five positive plaques were purified and the pBluescript plasmids containing the cloned DNA inserts were excised by co-infection with the helper phage. Each of the five positive clones contained DNA inserts of 2 to 3 kb (data not shown). The clone designated pYB2, which contains a 2.7 kb insert, was chosen for further study and a restriction map generated (FIG. 3). A series of nested deletions starting at either end of the 2.7 kb insert of pYB2 was performed using exonuclease III. Using overlapping deletion clones of pYB2, we determined 1969 bp sequence in both strands. As expected, the first 785 bases of this sequence (SEQ ID NO:3, beginning with nucleotide 2864) overlapped with the end of pMC3. Translation of the complete nucleotide sequence generated from pMC3, pYB1 and pYB2 in all possible reading frames revealed a single open reading frame of 3,543 nucleotides initiated by an ATG codon at position 1072 and terminated by a TAA codon at position 4,615. The sequence encodes a protein of 1181 amino acid residues (SEQ ID NO:4) and the calculated molecular weight of the deduced polypeptide is 131,517 daltons. A sequence that could form a potential stem-loop structure in the mRNA and which could serve as a transcription termination site ($\Delta G = -14.4$ Kcal) extends from nucleotides 4642 to 4674 (SEQ ID NO:3).

Homologies of the tagA polypeptide with other proteins.

Search of Swiss. Prot version 21, and NBRF-PIR protein data banks showed no striking homologies with the full length tagA antigen (SEQ ID NO:4). However, among the homologies with the highest scores were chloroplast $H^+$-transporting ATP synthases (Hiratsuka et al. *Mol. Gen. Genet.* 217:185-194, 1989; Rodermel and Bogorad *Genetics*, 116:127-139, 1987), and a sodium channel protein (Trimmer, et al. *Neuron* 3:33-49, 1989) with 16.8% and 17.3% identity, and 50% and 42.6% conserved amino acids in the region between residues 1-482 and 123-1182, respectively. No significant homologies were observed when the amino acid sequences of the other two ORFs contained in pMC3 were compared with the protein data bases.

The content of basic amino acids [141 lysines, (11.9%) and 117 asparagines (9.9%)] in the tagA product was unusually high and was consistent with the predicted isoelectric point of the peptide (8.89). A hydropathicity plot indicated that the deduced protein is predominantly hydrophilic. An interesting feature of the primary structure of this protein is the presence of structures of homopolymeric amino acid sequence, most notably polyasparagine (SEQ ID NO:4, Position 3705). In searches comparing this asparagine-rich region with various protein sequence data bases, there was strong homology with sequences from yeast (Forsburg and Guarente *Genes Dev.* 3:1166–1178, 1989; Hudspeth et al. *Cell* 30:617–626, 1982; Ju et al. *Mol. Cell. Biol.* 10:5226–5234, 1990; O'Hara et al. *Nucleic Acids Res.* 16:10133–10170, 1988; Rhode et al. Genes Dev. 3:1926–1939, 1989; Tanaka et al. *Mol. Cell. Biol.* 9:757–768, 1989; and Toda et al. *Genes Dev.* 2:517–527, 1988) and Plasmodium (Stahl et al. *Nucleic Acids Res.* 14:3089–3102, 1986) nucleotide-binding proteins. Polyasparagine is also found in the DNA-binding regulatory product of the lac9 gene of *Kluyveromyces var. lactis* (Salmeron and Johnston *Nucleic Acids Res.* 14:7767–7781, 1986) and potassium transport protein (TRK1) of *Saccharomyces cerevisiae* (Gaber et al. *Mol. Cell. Bio.* 8:2848–2859, 1989).

Construction of the full length tagA gene.

To construct the full length tagA gene, we utilized the unique SacI restriction site located in both pMC3 and pYB2 (FIG. 3). First, the 3.6 kb tagA fragment of pMC3 was cloned into a pUC19 vector under the control of the lacZ promoter, to generate pUT1. Next, the 2.6 kb SacI fragment from pYB2 was cloned into sacI-digested pUT1. A clone with the correct orientation was selected, which was named pUT2. An identical clone (pEM3), but present in the pGEM3z vector, has been deposited with the ATCC in compliance with the requirements of the Budapest Treaty under Accession No. 69273. *E. coli* cells containing pUT2 or pEM3 expressed the immunoreactive *H. pylori* 128 kDa protein.

Detection of human serologic responses to the recombinant tagA protein by Western blotting.

To determine whether human sera reacted with the full-length recombinant tagA protein, lysate from pEM3-containing cells was electrophoresed on a 7% acrylamide gel, and electroblotted onto nitrocellulose paper. Sera from 10 *H. pylori* infected humans and 10 uninfected humans were diluted 1:100 and tested for reactivity with the recombinant protein. Sera from 7 *H. pylori* infected persons recognized the tagA protein, compared to sera from 1 of 10 uninfected persons (p=0.01, one-tailed Fisher's exact test). Thus, the recombinant full-length protein was a useful antigen for assessing human responses to *H. pylori*.

Throughout this application various publications are referenced. The disclosures of these publications in their entireties are hereby incorporated by reference into this application in order to more fully describe the state of the art to which this invention pertains.

---

What is claimed is:

1. An isolated nucleic acid, consisting of nucleotides 1072 through 3648 contained in the nucleotide sequence defined in the Sequencing Listing as SEQ ID NO: 1.

2. A vector comprising the nucleic acid of claim 1.

3. A host cell comprising the vector of claim 2 for expressing the protein encoded by said sequence.

4. An isolated nucleic acid, consisting of nucleotides 1072 through 4614 contained in the nucleotide sequence defined in the Sequencing Listing as SEQ ID NO:3.

5. A vector comprising the nucleic acid of claim 4.

6. A host cell comprising the vector of claim 5 for expressing the protein encoded by said sequence.

* * * * *

UNITED STATES PATENT AND TRADEMARK OFFICE
CERTIFICATE OF CORRECTION

PATENT NO. : 5,403,924
DATED : April 4, 1995
INVENTOR(S) : Timothy L. Cover, et al It is certified that error appears in the above-indentified patent and that said Letters Patent is hereby corrected as shown below:

In column 1, line 6, please insert --This invention was made with government support awarded by the Medical Research Service of the Department of Veterans Affairs. The government has certain rights in the invention.--

Signed and Sealed this

Fifth Day of March, 1996

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 3648 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Helicobacter pylori ( i x ) FEATURE:
        ( A ) NAME/KEY: CDS
        ( B ) LOCATION: 1072..3648

( x i ) SEQUENCE DESCRIPTION: SEQ ID NO:1:

| | | | | | |
|---|---|---|---|---|---|
| ATGGGCTGCG | CGTAACGAAA | AACAGTCGCT | TGACCTCTTT | TGATGTCATC | AGAGATTTTC | 60 |
| CAAATATCCG | CTATACCTTT | GACTCCTAGA | GCGCAACCAC | CTACGATCGC | TAGAACAGAA | 120 |
| ATGATCTGAA | CCACCAAAGT | TTTAGTCTCA | GTAATGCCTG | ATGCAGGACT | GTCGAAAGCC | 180 |
| ATTAAAGGAT | TGGCTGCTAT | CGCTAGCCCT | AAAGTTACTA | CAACTTTCTT | GTAGCTGTCA | 240 |
| GTGATTCTTG | TAAAAAATTT | CATGCGTTTC | CTTTCAAATT | GAAATCAATC | GTTGAGTAT | 300 |
| ATCAAAAAAA | AGTATTTTTA | TACTATTCAT | ACAAGCGCTA | CTTTATAATT | TAAATCAAAA | 360 |
| CCGACGCTTT | TGTTTGACAA | CTGATATAAT | TTAGGAACAA | TAAACCTACT | TGTCCCAACC | 420 |
| ATTTTTCTTT | CTCAAGTCAT | CGTAGAATTG | TAGATCTTTA | GGATCTTTGA | TGTATTTTTT | 480 |
| AATCGTCTCA | GGTTGAAACC | TAAAACAAG | CAGAAACAAA | CCCAAGCTGA | TCAGAGTGAG | 540 |
| AATAAAGCTC | CATTTTAAGC | AACTCCATAA | ACCACTAAAG | AAACTTTTTT | TGAGACTCTC | 600 |
| TTTGAAAATC | TGTCCTATTG | ATTTGTTTTC | CATTTGTTT | CCCATGCGGA | TCACAAACGC | 660 |
| TTAATTACAA | ATACATACTA | TAATAAGTAT | GGCACACACA | AACCAAACCA | TTTTAGAAC | 720 |
| GCTTCATGCA | CTCACCTTGC | TCCTAACCAT | TTCTCCAACC | ATCTTTAGCG | TTGCATTTGA | 780 |
| TTTCTTCAAA | AAGGCTCATT | TCTTAGTTTC | TTTTATTCTT | AAAATTTTTC | CATTCTAGCA | 840 |
| AATTTTGTT | AATTGTGGGT | AAAAATGTGA | ATCGTTCCTA | GCTTTAGAC | GCTTGCAACG | 900 |
| ATCGGACTTT | TTTCAATATT | AATGAAAAA | TGCCAAATAT | TCTAAATATT | GTGGTATAGT | 960 |
| GATAACGTTC | AAAGACACGA | ATTGCATACT | CAAAGTGTGT | AGTAGTTTTT | AGCGGTCTTT | 1020 |
| GATACCAATA | AGATACCGAT | AGGTATGAAA | CTAGGTATAG | AAGGAGAAAC | A ATG ACT | 1077 |

Met Thr
                                                                                1

| AAC | GAA | ACT | ATT | GAC | CAA | CAA | CCA | CAA | ACC | GAA | GCG | GCT | TTT | AAC | CCG | 1125 |
|---|---|---|---|---|---|---|---|---|---|---|---|---|---|---|---|---|
| Asn | Glu | Thr | Ile | Asp | Gln | Gln | Pro | Gln | Thr | Glu | Ala | Ala | Phe | Asn | Pro | |
| | | 5 | | | | | 10 | | | | | 15 | | | | |

| CAG | CAA | TTT | ATC | AAT | AAT | CTT | CAA | GTA | GCT | TTT | CTT | AAA | GTT | GAT | AAC | 1173 |
|---|---|---|---|---|---|---|---|---|---|---|---|---|---|---|---|---|
| Gln | Gln | Phe | Ile | Asn | Asn | Leu | Gln | Val | Ala | Phe | Leu | Lys | Val | Asp | Asn | |
| 20 | | | | | 25 | | | | | 30 | | | | | | |

| GCT | GTC | GCT | TCA | TAC | GAT | CCT | GAT | CAA | AAA | CCA | ATC | GTT | GAT | AAG | AAC | 1221 |
|---|---|---|---|---|---|---|---|---|---|---|---|---|---|---|---|---|
| Ala | Val | Ala | Ser | Tyr | Asp | Pro | Asp | Gln | Lys | Pro | Ile | Val | Asp | Lys | Asn | |
| 35 | | | | 40 | | | | | 45 | | | | | | 50 | |

| GAT | AGG | GAT | AAC | AGG | CAA | GCT | TTT | GAG | GGA | ATC | TCG | CAA | TTA | AGG | GAA | 1269 |
|---|---|---|---|---|---|---|---|---|---|---|---|---|---|---|---|---|
| Asp | Arg | Asp | Asn | Arg | Gln | Ala | Phe | Glu | Gly | Ile | Ser | Gln | Leu | Arg | Glu | |
| | | | 55 | | | | | 60 | | | | | 65 | | | |

| GAA | TAC | TCC | AAT | AAA | GCG | ATC | AAA | AAT | CCT | ACC | AAA | AAG | AAT | CAG | TAT | 1317 |
|---|---|---|---|---|---|---|---|---|---|---|---|---|---|---|---|---|
| Glu | Tyr | Ser | Asn | Lys | Ala | Ile | Lys | Asn | Pro | Thr | Lys | Lys | Asn | Gln | Tyr | |
| | | | 70 | | | | | 75 | | | | | 80 | | | |

| TTT | TCA | GAC | TTT | ATC | AAT | AAG | AGC | AAT | GAT | TTA | ATC | AAC | AAA | GAC | AAT | 1365 |
|---|---|---|---|---|---|---|---|---|---|---|---|---|---|---|---|---|
| Phe | Ser | Asp | Phe | Ile | Asn | Lys | Ser | Asn | Asp | Leu | Ile | Asn | Lys | Asp | Asn | |
| | | 85 | | | | | 90 | | | | | 95 | | | | |

| CTC | ATT | GTC | GTG | GAA | TCT | TCC | ACA | AAG | AGC | TTT | CAG | AAA | TTT | GGG | GAT | 1413 |
|---|---|---|---|---|---|---|---|---|---|---|---|---|---|---|---|---|
| Leu | Ile | Val | Val | Glu | Ser | Ser | Thr | Lys | Ser | Phe | Gln | Lys | Phe | Gly | Asp | |
| | 100 | | | | | 105 | | | | | 110 | | | | | |

| CAG | CGT | TAC | CGA | ATT | TTC | ACA | AGT | TGG | GTG | TCC | CAT | CAA | AAC | GAT | CCG | 1461 |
|---|---|---|---|---|---|---|---|---|---|---|---|---|---|---|---|---|
| Gln | Arg | Tyr | Arg | Ile | Phe | Thr | Ser | Trp | Val | Ser | His | Gln | Asn | Asp | Pro | |
| 115 | | | | 120 | | | | | 125 | | | | | | 130 | |

| TCT | AAA | ATC | AAC | ACC | CGA | TGC | ATC | CGA | AAT | TTT | ATG | GAA | CAT | ACC | ATA | 1509 |
|---|---|---|---|---|---|---|---|---|---|---|---|---|---|---|---|---|
| Ser | Lys | Ile | Asn | Thr | Arg | Cys | Ile | Arg | Asn | Phe | Met | Glu | His | Thr | Ile | |
| | | | | 135 | | | | | 140 | | | | | | 145 | |

| CAA | CCC | CCT | ATC | CCT | GAT | GAC | AAA | GAA | AAA | GCA | GAG | TTT | TTG | AAA | TCT | 1557 |
|---|---|---|---|---|---|---|---|---|---|---|---|---|---|---|---|---|
| Gln | Pro | Pro | Ile | Pro | Asp | Asp | Lys | Glu | Lys | Ala | Glu | Phe | Leu | Lys | Ser | |
| | | | 150 | | | | | 155 | | | | | 160 | | | |

| GCC | AAA | CAA | TCT | TTT | GCA | GGA | ATC | ATC | ATA | GGG | AAT | CAA | ATC | CGA | ACG | 1605 |

```
Ala Lys Gln Ser Phe Ala Gly Ile Ile Ile Gly Asn Gln Ile Arg Thr
    165                 170                 175

GAT CAA AAA TTC ATG GGC GTG TTT GAT GAA TCC TTG AAA GAA AGG CAA        1653
Asp Gln Lys Phe Met Gly Val Phe Asp Glu Ser Leu Lys Glu Arg Gln
    180                 185                 190

GAA GCA GAA AAA AAT GGA GGG CCT ACT GGT GGG GAT TGG TTG GAT ATT        1701
Glu Ala Glu Lys Asn Gly Gly Pro Thr Gly Gly Asp Trp Leu Asp Ile
195                 200                 205                 210

TTT TTA TCA TTT ATA TTT GAC AAA AAA CAA TCT TCT GAT GTC AAA GAA        1749
Phe Leu Ser Phe Ile Phe Asp Lys Lys Gln Ser Ser Asp Val Lys Glu
                215                 220                 225

GCA ATC AAT CAA GAA CCA CTT CCT CAT GTC CAA CCA GAT ATA GCC ACT        1797
Ala Ile Asn Gln Glu Pro Leu Pro His Val Gln Pro Asp Ile Ala Thr
        230                 235                 240

AGC ACC ACT CAC ATA CAA GGC TTA CCG CCT GAA TCT AGG GAT TTG CTT        1845
Ser Thr Thr His Ile Gln Gly Leu Pro Pro Glu Ser Arg Asp Leu Leu
            245                 250                 255

GAT GAA AGG GGT AAT TTT TCT AAA TTC ACT CTT GGC GAT ATG GAA ATG        1893
Asp Glu Arg Gly Asn Phe Ser Lys Phe Thr Leu Gly Asp Met Glu Met
    260                 265                 270

TTA GAT GTT GAG GGC GTC GCC GAC ATG GAT CCC AAT TAC AAG TTC AAT        1941
Leu Asp Val Glu Gly Val Ala Asp Met Asp Pro Asn Tyr Lys Phe Asn
275                 280                 285                 290

CAA TTA TTG ATT CAC AAT AAC ACT CTG TCT TCT GTG TTA ATG GGG AGT        1989
Gln Leu Leu Ile His Asn Asn Thr Leu Ser Ser Val Leu Met Gly Ser
                295                 300                 305

CAT GAT GGC ATA GAA CCT GAA AAA GTT TCA TTA TTG TAT GCG GGC AAT        2037
His Asp Gly Ile Glu Pro Glu Lys Val Ser Leu Leu Tyr Ala Gly Asn
        310                 315                 320

GGT GGT TTT GGA GCC AAG CAC GAT TGG AAC GCC ACC GTT GGT TAT AAA        2085
Gly Gly Phe Gly Ala Lys His Asp Trp Asn Ala Thr Val Gly Tyr Lys
            325                 330                 335

GAC CAA CAA GGT AAC AAT GTG GCT ACA ATA ATT AAT GTG CAT ATG AAA        2133
Asp Gln Gln Gly Asn Asn Val Ala Thr Ile Ile Asn Val His Met Lys
    340                 345                 350

AAC GGC AGT GGC TTA GTC ATA GCA GGT GGT GAG AAA GGG ATT AAC AAC        2181
Asn Gly Ser Gly Leu Val Ile Ala Gly Gly Glu Lys Gly Ile Asn Asn
355                 360                 365                 370

CCT AGT TTT TAT CTC TAC AAA GAA GAC CAA CTC ACA GGC TCA CAA CGA        2229
Pro Ser Phe Tyr Leu Tyr Lys Glu Asp Gln Leu Thr Gly Ser Gln Arg
                375                 380                 385

GCA TTG AGT CAA GAA GAG ATC CAA AAC AAA ATA GAT TTC ATG GAA TTT        2277
Ala Leu Ser Gln Glu Glu Ile Gln Asn Lys Ile Asp Phe Met Glu Phe
        390                 395                 400

CTT GCA CAA AAC AAT GCT AAA TTA GAC AGC TTG AGC GAG AAA GAG AAA        2325
Leu Ala Gln Asn Asn Ala Lys Leu Asp Ser Leu Ser Glu Lys Glu Lys
            405                 410                 415

GAA AAA TTC CGA AAT GAG ATT AAG GAT TTC CAA AAA GAC TCT AAG CCT        2373
Glu Lys Phe Arg Asn Glu Ile Lys Asp Phe Gln Lys Asp Ser Lys Pro
    420                 425                 430

TAT TTA GAC GCC CTA GGG AAT GAT CGT ATT GCT TTT GTT TCT AAA AAA        2421
Tyr Leu Asp Ala Leu Gly Asn Asp Arg Ile Ala Phe Val Ser Lys Lys
435                 440                 445                 450

GAC CCA AAA CAT TCA GCT TTA ATT ACT GAG TTT AAT AAG GGG GAT TTG        2469
Asp Pro Lys His Ser Ala Leu Ile Thr Glu Phe Asn Lys Gly Asp Leu
                455                 460                 465

AGC TAC ACT CTC AAA GTT ATG GGA AAA AAG CAG ATA AAG GCT TTA GAT        2517
Ser Tyr Thr Leu Lys Val Met Gly Lys Lys Gln Ile Lys Ala Leu Asp
        470                 475                 480

AGG GAG AAA AAT GTC ACT CTT CAA GGT AAC CTA AAA CAT GAT GGC GTG        2565
Arg Glu Lys Asn Val Thr Leu Gln Gly Asn Leu Lys His Asp Gly Val
            485                 490                 495
```

| | | | | | | | | | | | | | | | | |
|---|---|---|---|---|---|---|---|---|---|---|---|---|---|---|---|---|
| ATG | TTT | GTT | AAT | TAT | TCT | AAT | TTC | AAA | TAC | ACC | AAC | GCC | TCC | AAG | AGT | 2613 |
| Met 500 | Phe | Val | Asn | Tyr | Ser 505 | Asn | Phe | Lys | Tyr | Thr 510 | Asn | Ala | Ser | Lys | Ser | |
| CCC | AAT | AAG | GGT | GTA | GGC | GTT | ACG | AAT | GGC | GTT | TCC | CAT | TTA | GAA | GCA | 2661 |
| Pro 515 | Asn | Lys | Gly | Val 520 | Gly | Val | Thr | Asn | Gly 525 | Val | Ser | His | Leu | Glu 530 | Ala | |
| GGC | TTT | AGC | AAG | GTG | GCT | GTC | TTT | AAT | TTG | CCT | AAT | TTA | AAT | AAT | CTC | 2709 |
| Gly | Phe | Ser | Lys | Val 535 | Ala | Val | Phe | Asn | Leu 540 | Pro | Asn | Leu | Asn | Asn 545 | Leu | |
| GCT | ATC | ACT | AGT | GTC | GTA | AGG | CGG | GAT | TTA | GAG | GAT | AAA | CTA | ATC | GCT | 2757 |
| Ala | Ile | Thr | Ser 550 | Val | Val | Arg | Arg | Asp 555 | Leu | Glu | Asp | Lys | Leu 560 | Ile | Ala | |
| AAA | GGA | TTG | TCC | CCA | CAA | GAA | GCT | AAT | AAG | CTT | GTC | AAA | GAT | TTT | TTG | 2805 |
| Lys | Gly | Leu | Ser 565 | Pro | Gln | Glu | Ala | Asn 570 | Lys | Leu | Val | Lys | Asp 575 | Phe | Leu | |
| AGT | AGC | AAC | AAA | GAA | TTG | GTT | GGA | AAA | GCT | TTA | AAC | TTC | AAT | AAA | GCT | 2853 |
| Ser | Ser | Asn 580 | Lys | Glu | Leu | Val | Gly 585 | Lys | Ala | Leu | Asn | Phe 590 | Asn | Lys | Ala | |
| GTA | GCT | GAA | GCT | AAA | AAC | ACA | GGC | AAC | TAT | GAC | GAG | GTG | AAA | CGA | GCT | 2901 |
| Val 595 | Ala | Glu | Ala | Lys | Asn 600 | Thr | Gly | Asn | Tyr | Asp 605 | Glu | Val | Lys | Arg | Ala 610 | |
| CAG | AAA | GAT | CTT | GAA | AAA | TCT | CTA | AAG | AAA | CGA | GAG | CAT | TTG | GAG | AAA | 2949 |
| Gln | Lys | Asp | Leu | Glu 615 | Lys | Ser | Leu | Lys | Lys 620 | Arg | Glu | His | Leu | Glu 625 | Lys | |
| GAT | GTA | GCG | AAA | AAT | TTG | GAG | AGC | AAA | AGC | GGC | AAC | AAA | AAT | AAA | ATG | 2997 |
| Asp | Val | Ala | Lys 630 | Asn | Leu | Glu | Ser | Lys 635 | Ser | Gly | Asn | Lys | Asn 640 | Lys | Met | |
| GAA | GCA | AAA | GCT | CAA | GCT | AAC | AGC | CAA | AAA | GAT | GAG | ATT | TTT | GCG | TTG | 3045 |
| Glu | Ala | Lys 645 | Ala | Gln | Ala | Asn | Ser 650 | Gln | Lys | Asp | Glu | Ile 655 | Phe | Ala | Leu | |
| ATC | AAT | AAA | GAG | GCT | AAT | AGA | GAC | GCA | AGA | GCA | ATC | GCT | TAC | GCT | CAA | 3093 |
| Ile | Asn | Lys | Glu 660 | Ala | Asn | Arg | Asp | Ala 665 | Arg | Ala | Ile | Ala | Tyr 670 | Ala | Gln | |
| AAT | CTT | AAA | GGC | ATC | AAA | AGG | GAA | TTG | TCT | GAT | AAA | CTT | GAA | AAT | ATC | 3141 |
| Asn 675 | Leu | Lys | Gly | Ile | Lys 680 | Arg | Glu | Leu | Ser | Asp 685 | Lys | Leu | Glu | Asn | Ile 690 | |
| AAC | AAG | GAT | TTG | AAA | GAC | TTT | AGT | AAA | TCT | TTT | GAT | GGA | TTC | AAA | AAT | 3189 |
| Asn | Lys | Asp | Leu | Lys 695 | Asp | Phe | Ser | Lys | Ser 700 | Phe | Asp | Gly | Phe | Lys 705 | Asn | |
| GGC | AAA | AAT | AAG | GAT | TTC | AGC | AAG | GCA | GAA | GAA | ACG | CTA | AAA | GCC | CTT | 3237 |
| Gly | Lys | Asn | Lys 710 | Asp | Phe | Ser | Lys | Ala 715 | Glu | Glu | Thr | Leu | Lys 720 | Ala | Leu | |
| AAA | GGC | TCG | GTG | AAA | GAT | TTA | GGT | ATC | AAT | CCG | GAA | TGG | ATT | TCA | AAA | 3285 |
| Lys | Gly | Ser 725 | Val | Lys | Asp | Leu | Gly 730 | Ile | Asn | Pro | Glu | Trp 735 | Ile | Ser | Lys | |
| GTT | GAA | AAC | CTT | AAT | GCA | GCT | TTG | AAT | GAA | TTC | AAA | AAT | GGC | AAA | AAT | 3333 |
| Val | Glu | Asn | Leu 740 | Asn | Ala | Ala | Leu | Asn 745 | Glu | Phe | Lys | Asn | Gly 750 | Lys | Asn | |
| AAG | GAT | TTC | AGC | AAG | GTA | ACG | CAA | GCA | AAA | AGC | GAC | CAA | GAA | AAT | TCC | 3381 |
| Lys 755 | Asp | Phe | Ser | Lys | Val 760 | Thr | Gln | Ala | Lys | Ser 765 | Asp | Gln | Glu | Asn | Ser 770 | |
| ATT | AAA | GAT | GTG | ATC | ATC | AAT | CAA | AAG | ATA | ACG | GAT | AAA | GTT | GAT | GAA | 3429 |
| Ile | Lys | Asp | Val | Ile 775 | Ile | Asn | Gln | Lys | Ile 780 | Thr | Asp | Lys | Val | Asp 785 | Glu | |
| CTC | AAT | CAA | GCG | GTA | TCA | GTG | GCT | AAA | ATA | GCG | TGC | GAT | TTC | AGT | GGG | 3477 |
| Leu | Asn | Gln | Ala | Val 790 | Ser | Val | Ala | Lys | Ile 795 | Ala | Cys | Asp | Phe | Ser 800 | Gly | |
| GTA | GAG | CAA | GCG | TTA | GCC | GAT | CTC | AAA | AAT | TTC | TCA | AAG | GAG | CAA | TTG | 3525 |
| Val | Glu | Gln | Ala | Leu 805 | Ala | Asp | Leu | Lys | Asn 810 | Phe | Ser | Lys | Glu | Gln 815 | Leu | |
| GCT | CAA | CAA | GCT | CAA | AAA | AAT | GAA | AGT | TTC | AAT | GTT | GGA | AAA | TCT | GAA | 3573 |

|     |     |     |     |     |     |     |     |     |     |     |     |     |     |     |      |
|-----|-----|-----|-----|-----|-----|-----|-----|-----|-----|-----|-----|-----|-----|-----|------|
| Ala | Gln | Gln | Ala | Gln | Lys | Asn | Glu | Ser | Phe | Asn | Val | Gly | Lys | Ser | Glu  |
|     | 820 |     |     |     | 825 |     |     |     |     |     | 830 |     |     |     |      |

| ATA | TAC | CAA | TCC | GTT | AAG | AAT | GGT | GTG | AAC | GGA | ACC | CTA | GTC | GGT | AAT | 3621 |
|-----|-----|-----|-----|-----|-----|-----|-----|-----|-----|-----|-----|-----|-----|-----|-----|------|
| Ile | Tyr | Gln | Ser | Val | Lys | Asn | Gly | Val | Asn | Gly | Thr | Leu | Val | Gly | Asn |      |
| 835 |     |     |     | 840 |     |     |     |     | 845 |     |     |     |     | 850 |     |      |

| GGG | TTA | TCT | GGA | ATA | GAG | GCC | ACA | GGG | 3648 |
|-----|-----|-----|-----|-----|-----|-----|-----|-----|------|
| Gly | Leu | Ser | Gly | Ile | Glu | Ala | Thr | Gly |      |
|     |     |     |     | 855 |     |     |     |     |      |

( 2 ) INFORMATION FOR SEQ ID NO:2:

( i ) SEQUENCE CHARACTERISTICS:
        ( A ) LENGTH: 859 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Thr | Asn | Glu | Thr | Ile | Asp | Gln | Gln | Pro | Gln | Thr | Glu | Ala | Ala | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asn | Pro | Gln | Gln | Phe | Ile | Asn | Asn | Leu | Gln | Val | Ala | Phe | Leu | Lys | Val |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asp | Asn | Ala | Val | Ala | Ser | Tyr | Asp | Pro | Asp | Gln | Lys | Pro | Ile | Val | Asp |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Lys | Asn | Asp | Arg | Asp | Asn | Arg | Gln | Ala | Phe | Glu | Gly | Ile | Ser | Gln | Leu |
|-----|-----|-----|-----|-----|-----|-----|-----|-----|-----|-----|-----|-----|-----|-----|-----|
| 50  |     |     |     |     | 55  |     |     |     |     | 60  |     |     |     |     |     |

| Arg | Glu | Glu | Tyr | Ser | Asn | Lys | Ala | Ile | Lys | Asn | Pro | Thr | Lys | Lys | Asn |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gln | Tyr | Phe | Ser | Asp | Phe | Ile | Asn | Lys | Ser | Asn | Asp | Leu | Ile | Asn | Lys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Asp | Asn | Leu | Ile | Val | Val | Glu | Ser | Ser | Thr | Lys | Ser | Phe | Gln | Lys | Phe |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Gly | Asp | Gln | Arg | Tyr | Arg | Ile | Phe | Thr | Ser | Trp | Val | Ser | His | Gln | Asn |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Asp | Pro | Ser | Lys | Ile | Asn | Thr | Arg | Cys | Ile | Arg | Asn | Phe | Met | Glu | His |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Thr | Ile | Gln | Pro | Pro | Ile | Pro | Asp | Asp | Lys | Glu | Lys | Ala | Glu | Phe | Leu |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Lys | Ser | Ala | Lys | Gln | Ser | Phe | Ala | Gly | Ile | Ile | Ile | Gly | Asn | Gln | Ile |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Arg | Thr | Asp | Gln | Lys | Phe | Met | Gly | Val | Phe | Asp | Glu | Ser | Leu | Lys | Glu |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Arg | Gln | Glu | Ala | Glu | Lys | Asn | Gly | Gly | Pro | Thr | Gly | Gly | Asp | Trp | Leu |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Asp | Ile | Phe | Leu | Ser | Phe | Ile | Phe | Asp | Lys | Lys | Gln | Ser | Ser | Asp | Val |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Lys | Glu | Ala | Ile | Asn | Gln | Glu | Pro | Leu | Pro | His | Val | Gln | Pro | Asp | Ile |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Ala | Thr | Ser | Thr | Thr | His | Ile | Gln | Gly | Leu | Pro | Pro | Glu | Ser | Arg | Asp |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Leu | Leu | Asp | Glu | Arg | Gly | Asn | Phe | Ser | Lys | Phe | Thr | Leu | Gly | Asp | Met |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Glu | Met | Leu | Asp | Val | Glu | Gly | Val | Ala | Asp | Met | Asp | Pro | Asn | Tyr | Lys |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Phe | Asn | Gln | Leu | Leu | Ile | His | Asn | Asn | Thr | Leu | Ser | Ser | Val | Leu | Met |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Gly | Ser | His | Asp | Gly | Ile | Glu | Pro | Glu | Lys | Val | Ser | Leu | Leu | Tyr | Ala |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

|  |  |  |  |  |  |  |  |  |  |  |  |  |  |
|---|---|---|---|---|---|---|---|---|---|---|---|---|---|
| Gly | Asn | Gly | Gly | Phe<br>325 | Gly | Ala | Lys | His<br>330 | Asp | Trp | Asn | Ala | Thr<br>335 | Val | Gly |
| Tyr | Lys | Asp | Gln<br>340 | Gln | Gly | Asn | Asn | Val<br>345 | Ala | Thr | Ile | Ile | Asn<br>350 | Val | His |
| Met | Lys | Asn<br>355 | Gly | Ser | Gly | Leu | Val<br>360 | Ile | Ala | Gly | Gly | Glu<br>365 | Lys | Gly | Ile |
| Asn | Asn<br>370 | Pro | Ser | Phe | Tyr | Leu<br>375 | Tyr | Lys | Glu | Asp | Gln<br>380 | Leu | Thr | Gly | Ser |
| Gln<br>385 | Arg | Ala | Leu | Ser | Gln<br>390 | Glu | Glu | Ile | Gln | Asn<br>395 | Lys | Ile | Asp | Phe | Met<br>400 |
| Glu | Phe | Leu | Ala | Gln<br>405 | Asn | Asn | Ala | Lys | Leu<br>410 | Asp | Ser | Leu | Ser | Glu<br>415 | Lys |
| Glu | Lys | Glu | Lys<br>420 | Phe | Arg | Asn | Glu | Ile<br>425 | Lys | Asp | Phe | Gln | Lys<br>430 | Asp | Ser |
| Lys | Pro | Tyr<br>435 | Leu | Asp | Ala | Leu | Gly<br>440 | Asn | Asp | Arg | Ile | Ala<br>445 | Phe | Val | Ser |
| Lys | Lys<br>450 | Asp | Pro | Lys | His | Ser<br>455 | Ala | Leu | Ile | Thr | Glu<br>460 | Phe | Asn | Lys | Gly |
| Asp<br>465 | Leu | Ser | Tyr | Thr | Leu<br>470 | Lys | Val | Met | Gly | Lys<br>475 | Lys | Gln | Ile | Lys | Ala<br>480 |
| Leu | Asp | Arg | Glu | Lys<br>485 | Asn | Val | Thr | Leu | Gln<br>490 | Gly | Asn | Leu | Lys | His<br>495 | Asp |
| Gly | Val | Met | Phe<br>500 | Val | Asn | Tyr | Ser | Asn<br>505 | Phe | Lys | Tyr | Thr | Asn<br>510 | Ala | Ser |
| Lys | Ser | Pro<br>515 | Asn | Lys | Gly | Val | Gly<br>520 | Val | Thr | Asn | Gly | Val<br>525 | Ser | His | Leu |
| Glu | Ala<br>530 | Gly | Phe | Ser | Lys | Val<br>535 | Ala | Val | Phe | Asn | Leu<br>540 | Pro | Asn | Leu | Asn |
| Asn<br>545 | Leu | Ala | Ile | Thr | Ser<br>550 | Val | Val | Arg | Arg | Asp<br>555 | Leu | Glu | Asp | Lys | Leu<br>560 |
| Ile | Ala | Lys | Gly | Leu<br>565 | Ser | Pro | Gln | Glu | Ala<br>570 | Asn | Lys | Leu | Val | Lys<br>575 | Asp |
| Phe | Leu | Ser | Ser<br>580 | Asn | Lys | Glu | Leu | Val<br>585 | Gly | Lys | Ala | Leu | Asn<br>590 | Phe | Asn |
| Lys | Ala | Val<br>595 | Ala | Glu | Ala | Lys | Asn<br>600 | Thr | Gly | Asn | Tyr | Asp<br>605 | Glu | Val | Lys |
| Arg | Ala<br>610 | Gln | Lys | Asp | Leu | Glu<br>615 | Lys | Ser | Leu | Lys | Lys<br>620 | Arg | Glu | His | Leu |
| Glu<br>625 | Lys | Asp | Val | Ala | Lys<br>630 | Asn | Leu | Glu | Ser | Lys<br>635 | Ser | Gly | Asn | Lys | Asn<br>640 |
| Lys | Met | Glu | Ala | Lys<br>645 | Ala | Gln | Ala | Asn | Ser<br>650 | Gln | Lys | Asp | Glu | Ile<br>655 | Phe |
| Ala | Leu | Ile | Asn<br>660 | Lys | Glu | Ala | Asn | Arg<br>665 | Asp | Ala | Arg | Ala | Ile<br>670 | Ala | Tyr |
| Ala | Gln | Asn<br>675 | Leu | Lys | Gly | Ile | Lys<br>680 | Arg | Glu | Leu | Ser | Asp<br>685 | Lys | Leu | Glu |
| Asn | Ile<br>690 | Asn | Lys | Asp | Leu | Lys<br>695 | Asp | Phe | Ser | Lys | Ser<br>700 | Phe | Asp | Gly | Phe |
| Lys<br>705 | Asn | Gly | Lys | Asn | Lys<br>710 | Asp | Phe | Ser | Lys | Ala<br>715 | Glu | Glu | Thr | Leu | Lys<br>720 |
| Ala | Leu | Lys | Gly | Ser<br>725 | Val | Lys | Asp | Leu | Gly<br>730 | Ile | Asn | Pro | Glu | Trp<br>735 | Ile |
| Ser | Lys | Val | Glu | Asn<br>740 | Leu | Asn | Ala | Ala | Leu<br>745 | Asn | Glu | Phe | Lys | Asn<br>750 | Gly |

-continued

| | | | | | | | | | | | | | |
|---|---|---|---|---|---|---|---|---|---|---|---|---|---|
| Lys | Asn | Lys<br>755 | Asp | Phe | Ser | Lys | Val<br>760 | Thr | Gln | Ala | Lys | Ser<br>765 | Asp | Gln | Glu |
| Asn | Ser | Ile<br>770 | Lys | Asp | Val | Ile<br>775 | Ile | Asn | Gln | Lys | Ile<br>780 | Thr | Asp | Lys | Val |
| Asp<br>785 | Glu | Leu | Asn | Gln<br>790 | Ala | Val | Ser | Val | Ala<br>795 | Lys | Ile | Ala | Cys | Asp | Phe<br>800 |
| Ser | Gly | Val | Glu | Gln<br>805 | Ala | Leu | Ala | Asp | Leu<br>810 | Lys | Asn | Phe | Ser | Lys<br>815 | Glu |
| Gln | Leu | Ala | Gln<br>820 | Gln | Ala | Gln | Lys | Asn<br>825 | Glu | Ser | Phe | Asn | Val<br>830 | Gly | Lys |
| Ser | Glu | Ile<br>835 | Tyr | Gln | Ser | Val | Lys<br>840 | Asn | Gly | Val | Asn | Gly<br>845 | Thr | Leu | Val |
| Gly | Asn | Gly<br>850 | Leu | Ser | Gly | Ile<br>855 | Glu | Ala | Thr | Gly | | | | | |

( 2 ) INFORMATION FOR SEQ ID NO:3:

( i ) SEQUENCE CHARACTERISTICS:
        ( A ) LENGTH: 4821 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1072..4614

( x i ) SEQUENCE DESCRIPTION: SEQ ID NO:3:

```
ATGGGCTGCG CGTAACGAAA AACAGTCGCT TGACCTCTTT TGATGTCATC AGAGATTTTC      60
CAAATATCCG CTATACCTTT GACTCCTAGA GCGCAACCAC CTACGATCGC TAGAACAGAA     120
ATGATCTGAA CCACCAAAGT TTAGTCTCA  GTAATGCCTG ATGCAGGACT GTCGAAAGCC     180
ATTAAAGGAT TGGCTGCTAT CGCTAGCCCT AAAGTTACTA CAACTTTCTT GTAGCTGTCA     240
GTGATTCTTG TAAAAAATTT CATGCGTTTC CTTTCAAATT GAAATCAATC GTTTGAGTAT     300
ATCAAAAAAA AGTATTTTTA TACTATTCAT ACAAGCGCTA CTTTATAATT TAAATCAAAA     360
CCGACGCTTT TGTTTGACAA CTGATATAAT TTAGGAACAA TAAACCTACT TGTCCCAACC     420
ATTTTTCTTT CTCAAGTCAT CGTAGAATTG TAGATCTTTA GGATCTTTGA TGTATTTTTT     480
AATCGTCTCA GGTTGAAACC TAAAAACAAG CAGAAACAAA CCCAAGCTGA TCAGAGTGAG     540
AATAAAGCTC CATTTTAAGC AACTCCATAA ACCACTAAAG AAACTTTTTT TGAGACTCTC     600
TTTGAAAATC TGTCCTATTG ATTTGTTTC  CATTTTGTTT CCCATGCGGA TCACAAACGC     660
TTAATTACAA ATACATACTA TAATAAGTAT GGCACACACA AACCAAACCA TTTTTAGAAC     720
GCTTCATGCA CTCACCTTGC TCCTAACCAT TTCTCCAACC ATCTTTAGCG TTGCATTTGA     780
TTTCTTCAAA AAGGCTCATT TCTTAGTTTC TTTTATTCTT AAAATTTTTC CATTCTAGCA     840
AATTTTTGTT AATTGTGGGT AAAAATGTGA ATCGTTCCTA GCTTTAGAC  GCTTGCAACG     900
ATCGGACTTT TTTCAATATT AATGAAAAAA TGCCAAATAT TCTAAATATT GTGGTATAGT     960
GATAACGTTC AAAGACACGA ATTGCATACT CAAAGTGTGT AGTAGTTTTT AGCGGTCTTT    1020
GATACCAATA AGATACCGAT AGGTATGAAA CTAGGTATAG AAGGAGAAAC A ATG ACT    1077
                                                            Met Thr
                                                              1

AAC GAA ACT ATT GAC CAA CAA CCA CAA ACC GAA GCG GCT TTT AAC CCG      1125
Asn Glu Thr Ile Asp Gln Gln Pro Gln Thr Glu Ala Ala Phe Asn Pro
       5                  10                  15

CAG CAA TTT ATC AAT AAT CTT CAA GTA GCT TTT CTT AAA GTT GAT AAC      1173
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | Gln | Gln | Phe | Ile | Asn | Asn | Leu | Gln | Val | Ala | Phe | Leu | Lys | Val | Asp | Asn  |
|     |     | 20  |     |     |     | 25  |     |     |     | 30  |     |     |     |     |     |      |
| GCT | GTC | GCT | TCA | TAC | GAT | CCT | GAT | CAA | AAA | CCA | ATC | GTT | GAT | AAG | AAC | 1221 |
| Ala | Val | Ala | Ser | Tyr | Asp | Pro | Asp | Gln | Lys | Pro | Ile | Val | Asp | Lys | Asn |      |
| 35  |     |     |     | 40  |     |     |     |     | 45  |     |     |     |     |     | 50  |      |
| GAT | AGG | GAT | AAC | AGG | CAA | GCT | TTT | GAG | GGA | ATC | TCG | CAA | TTA | AGG | GAA | 1269 |
| Asp | Arg | Asp | Asn | Arg | Gln | Ala | Phe | Glu | Gly | Ile | Ser | Gln | Leu | Arg | Glu |      |
|     |     |     |     | 55  |     |     |     |     | 60  |     |     |     |     | 65  |     |      |
| GAA | TAC | TCC | AAT | AAA | GCG | ATC | AAA | AAT | CCT | ACC | AAA | AAG | AAT | CAG | TAT | 1317 |
| Glu | Tyr | Ser | Asn | Lys | Ala | Ile | Lys | Asn | Pro | Thr | Lys | Lys | Asn | Gln | Tyr |      |
|     |     |     | 70  |     |     |     |     | 75  |     |     |     |     | 80  |     |     |      |
| TTT | TCA | GAC | TTT | ATC | AAT | AAG | AGC | AAT | GAT | TTA | ATC | AAC | AAA | GAC | AAT | 1365 |
| Phe | Ser | Asp | Phe | Ile | Asn | Lys | Ser | Asn | Asp | Leu | Ile | Asn | Lys | Asp | Asn |      |
|     |     | 85  |     |     |     |     | 90  |     |     |     |     | 95  |     |     |     |      |
| CTC | ATT | GTC | GTG | GAA | TCT | TCC | ACA | AAG | AGC | TTT | CAG | AAA | TTT | GGG | GAT | 1413 |
| Leu | Ile | Val | Val | Glu | Ser | Ser | Thr | Lys | Ser | Phe | Gln | Lys | Phe | Gly | Asp |      |
|     | 100 |     |     |     |     | 105 |     |     |     |     | 110 |     |     |     |     |      |
| CAG | CGT | TAC | CGA | ATT | TTC | ACA | AGT | TGG | GTG | TCC | CAT | CAA | AAC | GAT | CCG | 1461 |
| Gln | Arg | Tyr | Arg | Ile | Phe | Thr | Ser | Trp | Val | Ser | His | Gln | Asn | Asp | Pro |      |
| 115 |     |     |     |     | 120 |     |     |     |     | 125 |     |     |     |     | 130 |      |
| TCT | AAA | ATC | AAC | ACC | CGA | TGC | ATC | CGA | AAT | TTT | ATG | GAA | CAT | ACC | ATA | 1509 |
| Ser | Lys | Ile | Asn | Thr | Arg | Cys | Ile | Arg | Asn | Phe | Met | Glu | His | Thr | Ile |      |
|     |     |     |     | 135 |     |     |     |     | 140 |     |     |     |     | 145 |     |      |
| CAA | CCC | CCT | ATC | CCT | GAT | GAC | AAA | GAA | AAA | GCA | GAG | TTT | TTG | AAA | TCT | 1557 |
| Gln | Pro | Pro | Ile | Pro | Asp | Asp | Lys | Glu | Lys | Ala | Glu | Phe | Leu | Lys | Ser |      |
|     |     |     | 150 |     |     |     |     | 155 |     |     |     |     | 160 |     |     |      |
| GCC | AAA | CAA | TCT | TTT | GCA | GGA | ATC | ATC | ATA | GGG | AAT | CAA | ATC | CGA | ACG | 1605 |
| Ala | Lys | Gln | Ser | Phe | Ala | Gly | Ile | Ile | Ile | Gly | Asn | Gln | Ile | Arg | Thr |      |
|     | 165 |     |     |     |     | 170 |     |     |     |     | 175 |     |     |     |     |      |
| GAT | CAA | AAA | TTC | ATG | GGC | GTG | TTT | GAT | GAA | TCC | TTG | AAA | GAA | AGG | CAA | 1653 |
| Asp | Gln | Lys | Phe | Met | Gly | Val | Phe | Asp | Glu | Ser | Leu | Lys | Glu | Arg | Gln |      |
|     | 180 |     |     |     |     | 185 |     |     |     |     | 190 |     |     |     |     |      |
| GAA | GCA | GAA | AAA | AAT | GGA | GGG | CCT | ACT | GGT | GGG | GAT | TGG | TTG | GAT | ATT | 1701 |
| Glu | Ala | Glu | Lys | Asn | Gly | Gly | Pro | Thr | Gly | Gly | Asp | Trp | Leu | Asp | Ile |      |
| 195 |     |     |     |     | 200 |     |     |     |     | 205 |     |     |     |     | 210 |      |
| TTT | TTA | TCA | TTT | ATA | TTT | GAC | AAA | AAA | CAA | TCT | TCT | GAT | GTC | AAA | GAA | 1749 |
| Phe | Leu | Ser | Phe | Ile | Phe | Asp | Lys | Lys | Gln | Ser | Ser | Asp | Val | Lys | Glu |      |
|     |     |     |     | 215 |     |     |     |     | 220 |     |     |     |     | 225 |     |      |
| GCA | ATC | AAT | CAA | GAA | CCA | CTT | CCT | CAT | GTC | CAA | CCA | GAT | ATA | GCC | ACT | 1797 |
| Ala | Ile | Asn | Gln | Glu | Pro | Leu | Pro | His | Val | Gln | Pro | Asp | Ile | Ala | Thr |      |
|     |     |     | 230 |     |     |     |     | 235 |     |     |     |     | 240 |     |     |      |
| AGC | ACC | ACT | CAC | ATA | CAA | GGC | TTA | CCG | CCT | GAA | TCT | AGG | GAT | TTG | CTT | 1845 |
| Ser | Thr | Thr | His | Ile | Gln | Gly | Leu | Pro | Pro | Glu | Ser | Arg | Asp | Leu | Leu |      |
|     |     | 245 |     |     |     |     | 250 |     |     |     |     | 255 |     |     |     |      |
| GAT | GAA | AGG | GGT | AAT | TTT | TCT | AAA | TTC | ACT | CTT | GGC | GAT | ATG | GAA | ATG | 1893 |
| Asp | Glu | Arg | Gly | Asn | Phe | Ser | Lys | Phe | Thr | Leu | Gly | Asp | Met | Glu | Met |      |
|     | 260 |     |     |     |     | 265 |     |     |     |     | 270 |     |     |     |     |      |
| TTA | GAT | GTT | GAG | GGC | GTC | GCC | GAC | ATG | GAT | CCC | AAT | TAC | AAG | TTC | AAT | 1941 |
| Leu | Asp | Val | Glu | Gly | Val | Ala | Asp | Met | Asp | Pro | Asn | Tyr | Lys | Phe | Asn |      |
| 275 |     |     |     |     | 280 |     |     |     |     | 285 |     |     |     |     | 290 |      |
| CAA | TTA | TTG | ATT | CAC | AAT | AAC | ACT | CTG | TCT | TCT | GTG | TTA | ATG | GGG | AGT | 1989 |
| Gln | Leu | Leu | Ile | His | Asn | Asn | Thr | Leu | Ser | Ser | Val | Leu | Met | Gly | Ser |      |
|     |     |     |     | 295 |     |     |     |     | 300 |     |     |     |     | 305 |     |      |
| CAT | GAT | GGC | ATA | GAA | CCT | GAA | AAA | GTT | TCA | TTA | TTG | TAT | GCG | GGC | AAT | 2037 |
| His | Asp | Gly | Ile | Glu | Pro | Glu | Lys | Val | Ser | Leu | Leu | Tyr | Ala | Gly | Asn |      |
|     |     |     | 310 |     |     |     |     | 315 |     |     |     |     | 320 |     |     |      |
| GGT | GGT | TTT | GGA | GCC | AAG | CAC | GAT | TGG | AAC | GCC | ACC | GTT | GGT | TAT | AAA | 2085 |
| Gly | Gly | Phe | Gly | Ala | Lys | His | Asp | Trp | Asn | Ala | Thr | Val | Gly | Tyr | Lys |      |
|     |     | 325 |     |     |     |     | 330 |     |     |     |     | 335 |     |     |     |      |
| GAC | CAA | CAA | GGT | AAC | AAT | GTG | GCT | ACA | ATA | ATT | AAT | GTG | CAT | ATG | AAA | 2133 |
| Asp | Gln | Gln | Gly | Asn | Asn | Val | Ala | Thr | Ile | Ile | Asn | Val | His | Met | Lys |      |
|     | 340 |     |     |     |     | 345 |     |     |     |     | 350 |     |     |     |     |      |

| | | | | | | | | | | | | | | | | |
|---|---|---|---|---|---|---|---|---|---|---|---|---|---|---|---|---|
| AAC | GGC | AGT | GGC | TTA | GTC | ATA | GCA | GGT | GGT | GAG | AAA | GGG | ATT | AAC | AAC | 2181 |
| Asn | Gly | Ser | Gly | Leu | Val | Ile | Ala | Gly | Gly | Glu | Lys | Gly | Ile | Asn | Asn | |
| 355 | | | | 360 | | | | | 365 | | | | | | 370 | |
| CCT | AGT | TTT | TAT | CTC | TAC | AAA | GAA | GAC | CAA | CTC | ACA | GGC | TCA | CAA | CGA | 2229 |
| Pro | Ser | Phe | Tyr | Leu | Tyr | Lys | Glu | Asp | Gln | Leu | Thr | Gly | Ser | Gln | Arg | |
| | | | | 375 | | | | | 380 | | | | | 385 | | |
| GCA | TTG | AGT | CAA | GAA | GAG | ATC | CAA | AAC | AAA | ATA | GAT | TTC | ATG | GAA | TTT | 2277 |
| Ala | Leu | Ser | Gln | Glu | Glu | Ile | Gln | Asn | Lys | Ile | Asp | Phe | Met | Glu | Phe | |
| | | | 390 | | | | | 395 | | | | | 400 | | | |
| CTT | GCA | CAA | AAC | AAT | GCT | AAA | TTA | GAC | AGC | TTG | AGC | GAG | AAA | GAG | AAA | 2325 |
| Leu | Ala | Gln | Asn | Asn | Ala | Lys | Leu | Asp | Ser | Leu | Ser | Glu | Lys | Glu | Lys | |
| | | | 405 | | | | 410 | | | | | 415 | | | | |
| GAA | AAA | TTC | CGA | AAT | GAG | ATT | AAG | GAT | TTC | CAA | AAA | GAC | TCT | AAG | CCT | 2373 |
| Glu | Lys | Phe | Arg | Asn | Glu | Ile | Lys | Asp | Phe | Gln | Lys | Asp | Ser | Lys | Pro | |
| | 420 | | | | | 425 | | | | | 430 | | | | | |
| TAT | TTA | GAC | GCC | CTA | GGG | AAT | GAT | CGT | ATT | GCT | TTT | GTT | TCT | AAA | AAA | 2421 |
| Tyr | Leu | Asp | Ala | Leu | Gly | Asn | Asp | Arg | Ile | Ala | Phe | Val | Ser | Lys | Lys | |
| 435 | | | | 440 | | | | | 445 | | | | | | 450 | |
| GAC | CCA | AAA | CAT | TCA | GCT | TTA | ATT | ACT | GAG | TTT | AAT | AAG | GGG | GAT | TTG | 2469 |
| Asp | Pro | Lys | His | Ser | Ala | Leu | Ile | Thr | Glu | Phe | Asn | Lys | Gly | Asp | Leu | |
| | | | | 455 | | | | | 460 | | | | | 465 | | |
| AGC | TAC | ACT | CTC | AAA | GTT | ATG | GGA | AAA | AAG | CAG | ATA | AAG | GCT | TTA | GAT | 2517 |
| Ser | Tyr | Thr | Leu | Lys | Val | Met | Gly | Lys | Lys | Gln | Ile | Lys | Ala | Leu | Asp | |
| | | | 470 | | | | | 475 | | | | | 480 | | | |
| AGG | GAG | AAA | AAT | GTC | ACT | CTT | CAA | GGT | AAC | CTA | AAA | CAT | GAT | GGC | GTG | 2565 |
| Arg | Glu | Lys | Asn | Val | Thr | Leu | Gln | Gly | Asn | Leu | Lys | His | Asp | Gly | Val | |
| | | 485 | | | | | 490 | | | | | 495 | | | | |
| ATG | TTT | GTT | AAT | TAT | TCT | AAT | TTC | AAA | TAC | ACC | AAC | GCC | TCC | AAG | AGT | 2613 |
| Met | Phe | Val | Asn | Tyr | Ser | Asn | Phe | Lys | Tyr | Thr | Asn | Ala | Ser | Lys | Ser | |
| | 500 | | | | 505 | | | | | 510 | | | | | | |
| CCC | AAT | AAG | GGT | GTA | GGC | GTT | ACG | AAT | GGC | GTT | TCC | CAT | TTA | GAA | GCA | 2661 |
| Pro | Asn | Lys | Gly | Val | Gly | Val | Thr | Asn | Gly | Val | Ser | His | Leu | Glu | Ala | |
| 515 | | | | 520 | | | | | 525 | | | | | | 530 | |
| GGC | TTT | AGC | AAG | GTG | GCT | GTC | TTT | AAT | TTG | CCT | AAT | TTA | AAT | AAT | CTC | 2709 |
| Gly | Phe | Ser | Lys | Val | Ala | Val | Phe | Asn | Leu | Pro | Asn | Leu | Asn | Asn | Leu | |
| | | | | 535 | | | | | 540 | | | | | 545 | | |
| GCT | ATC | ACT | AGT | GTC | GTA | AGG | CGG | GAT | TTA | GAG | GAT | AAA | CTA | ATC | GCT | 2757 |
| Ala | Ile | Thr | Ser | Val | Val | Arg | Arg | Asp | Leu | Glu | Asp | Lys | Leu | Ile | Ala | |
| | | | 550 | | | | | 555 | | | | | 560 | | | |
| AAA | GGA | TTG | TCC | CCA | CAA | GAA | GCT | AAT | AAG | CTT | GTC | AAA | GAT | TTT | TTG | 2805 |
| Lys | Gly | Leu | Ser | Pro | Gln | Glu | Ala | Asn | Lys | Leu | Val | Lys | Asp | Phe | Leu | |
| | | 565 | | | | | 570 | | | | | 575 | | | | |
| AGT | AGC | AAC | AAA | GAA | TTG | GTT | GGA | AAA | GCT | TTA | AAC | TTC | AAT | AAA | GCT | 2853 |
| Ser | Ser | Asn | Lys | Glu | Leu | Val | Gly | Lys | Ala | Leu | Asn | Phe | Asn | Lys | Ala | |
| | 580 | | | | | 585 | | | | | 590 | | | | | |
| GTA | GCT | GAA | GCT | AAA | AAC | ACA | GGC | AAC | TAT | GAC | GAG | GTG | AAA | CGA | GCT | 2901 |
| Val | Ala | Glu | Ala | Lys | Asn | Thr | Gly | Asn | Tyr | Asp | Glu | Val | Lys | Arg | Ala | |
| 595 | | | | | 600 | | | | | 605 | | | | | 610 | |
| CAG | AAA | GAT | CTT | GAA | AAA | TCT | CTA | AAG | AAA | CGA | GAG | CAT | TTG | GAG | AAG | 2949 |
| Gln | Lys | Asp | Leu | Glu | Lys | Ser | Leu | Lys | Lys | Arg | Glu | His | Leu | Glu | Lys | |
| | | | | 615 | | | | 620 | | | | | 625 | | | |
| GAT | GTA | GCG | AAA | AAT | TTG | GAG | AGC | AAA | AGC | GGC | AAC | AAA | AAT | AAA | ATG | 2997 |
| Asp | Val | Ala | Lys | Asn | Leu | Glu | Ser | Lys | Ser | Gly | Asn | Lys | Asn | Lys | Met | |
| | | | 630 | | | | | 635 | | | | | 640 | | | |
| GAA | GCA | AAA | GCT | CAA | GCT | AAC | AGC | CAA | AAA | GAT | GAG | ATT | TTT | GCG | TTG | 3045 |
| Glu | Ala | Lys | Ala | Gln | Ala | Asn | Ser | Gln | Lys | Asp | Glu | Ile | Phe | Ala | Leu | |
| | | 645 | | | | | 650 | | | | | 655 | | | | |
| ATC | AAT | AAA | GAG | GCT | AAT | AGA | GAC | GCA | AGA | GCA | ATC | GCT | TAC | GCT | CAA | 3093 |
| Ile | Asn | Lys | Glu | Ala | Asn | Arg | Asp | Ala | Arg | Ala | Ile | Ala | Tyr | Ala | Gln | |
| | | 660 | | | | | 665 | | | | | 670 | | | | |
| AAT | CTT | AAA | GGC | ATC | AAA | AGG | GAA | TTG | TCT | GAT | AAA | CTT | GAA | AAT | ATC | 3141 |

|   |   |   |   |   |   |   |   |   |   |   |   |   |   |   |   |
|---|---|---|---|---|---|---|---|---|---|---|---|---|---|---|---|
| Asn | Leu | Lys | Gly | Ile | Lys | Arg | Glu | Leu | Ser | Asp | Lys | Leu | Glu | Asn | Ile |
| 675 |   |   |   |   | 680 |   |   |   |   | 685 |   |   |   |   | 690 |

| AAC | AAG | GAT | TTG | AAA | GAC | TTT | AGT | AAA | TCT | TTT | GAT | GGA | TTC | AAA | AAT | 3189 |
|---|---|---|---|---|---|---|---|---|---|---|---|---|---|---|---|---|
| Asn | Lys | Asp | Leu | Lys | Asp | Phe | Ser | Lys | Ser | Phe | Asp | Gly | Phe | Lys | Asn |   |
|   |   |   |   | 695 |   |   |   |   | 700 |   |   |   |   | 705 |   |   |

| GGC | AAA | AAT | AAG | GAT | TTC | AGC | AAG | GCA | GAA | GAA | ACG | CTA | AAA | GCC | CTT | 3237 |
|---|---|---|---|---|---|---|---|---|---|---|---|---|---|---|---|---|
| Gly | Lys | Asn | Lys | Asp | Phe | Ser | Lys | Ala | Glu | Glu | Thr | Leu | Lys | Ala | Leu |   |
|   |   |   | 710 |   |   |   |   | 715 |   |   |   |   | 720 |   |   |   |

| AAA | GGC | TCG | GTG | AAA | GAT | TTA | GGT | ATC | AAT | CCG | GAA | TGG | ATT | TCA | AAA | 3285 |
|---|---|---|---|---|---|---|---|---|---|---|---|---|---|---|---|---|
| Lys | Gly | Ser | Val | Lys | Asp | Leu | Gly | Ile | Asn | Pro | Glu | Trp | Ile | Ser | Lys |   |
|   |   | 725 |   |   |   |   | 730 |   |   |   |   | 735 |   |   |   |   |

| GTT | GAA | AAC | CTT | AAT | GCA | GCT | TTG | AAT | GAA | TTC | AAA | AAT | GGC | AAA | AAT | 3333 |
|---|---|---|---|---|---|---|---|---|---|---|---|---|---|---|---|---|
| Val | Glu | Asn | Leu | Asn | Ala | Ala | Leu | Asn | Glu | Phe | Lys | Asn | Gly | Lys | Asn |   |
|   |   | 740 |   |   |   | 745 |   |   |   |   | 750 |   |   |   |   |   |

| AAG | GAT | TTC | AGC | AAG | GTA | ACG | CAA | GCA | AAA | AGC | GAC | CAA | GAA | AAT | TCC | 3381 |
|---|---|---|---|---|---|---|---|---|---|---|---|---|---|---|---|---|
| Lys | Asp | Phe | Ser | Lys | Val | Thr | Gln | Ala | Lys | Ser | Asp | Gln | Glu | Asn | Ser |   |
| 755 |   |   |   |   | 760 |   |   |   |   | 765 |   |   |   |   | 770 |   |

| ATT | AAA | GAT | GTG | ATC | ATC | AAT | CAA | AAG | ATA | ACG | GAT | AAA | GTT | GAT | GAA | 3429 |
|---|---|---|---|---|---|---|---|---|---|---|---|---|---|---|---|---|
| Ile | Lys | Asp | Val | Ile | Ile | Asn | Gln | Lys | Ile | Thr | Asp | Lys | Val | Asp | Glu |   |
|   |   |   |   | 775 |   |   |   |   | 780 |   |   |   |   | 785 |   |   |

| CTC | AAT | CAA | GCG | GTA | TCA | GTG | GCT | AAA | ATA | GCG | TGC | GAT | TTC | AGT | GGG | 3477 |
|---|---|---|---|---|---|---|---|---|---|---|---|---|---|---|---|---|
| Leu | Asn | Gln | Ala | Val | Ser | Val | Ala | Lys | Ile | Ala | Cys | Asp | Phe | Ser | Gly |   |
|   |   |   | 790 |   |   |   |   | 795 |   |   |   |   | 800 |   |   |   |

| GTA | GAG | CAA | GCG | TTA | GCC | GAT | CTC | AAA | AAT | TTC | TCA | AAG | GAG | CAA | TTG | 3525 |
|---|---|---|---|---|---|---|---|---|---|---|---|---|---|---|---|---|
| Val | Glu | Gln | Ala | Leu | Ala | Asp | Leu | Lys | Asn | Phe | Ser | Lys | Glu | Gln | Leu |   |
|   |   | 805 |   |   |   |   | 810 |   |   |   |   | 815 |   |   |   |   |

| GCT | CAA | CAA | GCT | CAA | AAA | AAT | GAA | AGT | TTC | AAT | GTT | GGA | AAA | TCT | GAA | 3573 |
|---|---|---|---|---|---|---|---|---|---|---|---|---|---|---|---|---|
| Ala | Gln | Gln | Ala | Gln | Lys | Asn | Glu | Ser | Phe | Asn | Val | Gly | Lys | Ser | Glu |   |
|   | 820 |   |   |   |   | 825 |   |   |   |   | 830 |   |   |   |   |   |

| ATA | TAC | CAA | TCC | GTT | AAG | AAT | GGT | GTG | AAC | GGA | ACC | CTA | GTC | GGT | AAT | 3621 |
|---|---|---|---|---|---|---|---|---|---|---|---|---|---|---|---|---|
| Ile | Tyr | Gln | Ser | Val | Lys | Asn | Gly | Val | Asn | Gly | Thr | Leu | Val | Gly | Asn |   |
| 835 |   |   |   |   | 840 |   |   |   |   | 845 |   |   |   |   | 850 |   |

| GGG | TTA | TCT | GGA | ATA | GAG | GCC | ACA | GCT | CTC | GCC | AAA | AAT | TTT | TCG | GAT | 3669 |
|---|---|---|---|---|---|---|---|---|---|---|---|---|---|---|---|---|
| Gly | Leu | Ser | Gly | Ile | Glu | Ala | Thr | Ala | Leu | Ala | Lys | Asn | Phe | Ser | Asp |   |
|   |   |   |   | 855 |   |   |   |   | 860 |   |   |   |   | 865 |   |   |

| ATC | AAG | AAA | GAA | TTG | AAT | GAG | AAA | TTT | AAA | AAT | TTC | AAT | AAC | AAT | AAC | 3717 |
|---|---|---|---|---|---|---|---|---|---|---|---|---|---|---|---|---|
| Ile | Lys | Lys | Glu | Leu | Asn | Glu | Lys | Phe | Lys | Asn | Phe | Asn | Asn | Asn | Asn |   |
|   |   |   | 870 |   |   |   |   | 875 |   |   |   |   | 880 |   |   |   |

| AAT | AAT | GGT | CTC | AAA | AAC | GGC | GGA | GAA | CCC | ATT | TAT | GCT | CAA | GTT | AAT | 3765 |
|---|---|---|---|---|---|---|---|---|---|---|---|---|---|---|---|---|
| Asn | Asn | Gly | Leu | Lys | Asn | Gly | Gly | Glu | Pro | Ile | Tyr | Ala | Gln | Val | Asn |   |
|   |   | 885 |   |   |   |   | 890 |   |   |   |   | 895 |   |   |   |   |

| AAA | AAG | AAA | ACA | GGA | CAA | GTA | GCT | AGC | CCT | GAA | GAA | CCC | ATT | TAT | GCT | 3813 |
|---|---|---|---|---|---|---|---|---|---|---|---|---|---|---|---|---|
| Lys | Lys | Lys | Thr | Gly | Gln | Val | Ala | Ser | Pro | Glu | Glu | Pro | Ile | Tyr | Ala |   |
|   | 900 |   |   |   |   | 905 |   |   |   |   | 910 |   |   |   |   |   |

| CAA | GTT | GCT | AAA | AAG | GTA | ACT | AAA | AAA | ATT | GAC | CAA | CTC | AAT | CAA | GCA | 3861 |
|---|---|---|---|---|---|---|---|---|---|---|---|---|---|---|---|---|
| Gln | Val | Ala | Lys | Lys | Val | Thr | Lys | Lys | Ile | Asp | Gln | Leu | Asn | Gln | Ala |   |
| 915 |   |   |   |   | 920 |   |   |   |   | 925 |   |   |   |   | 930 |   |

| GCG | ACA | AGT | GGT | TTC | GGT | GGT | GTA | GGG | CAA | GCG | GGC | TTC | CCT | TTG | AAA | 3909 |
|---|---|---|---|---|---|---|---|---|---|---|---|---|---|---|---|---|
| Ala | Thr | Ser | Gly | Phe | Gly | Gly | Val | Gly | Gln | Ala | Gly | Phe | Pro | Leu | Lys |   |
|   |   |   |   | 935 |   |   |   |   | 940 |   |   |   |   | 945 |   |   |

| AGG | CAT | GAT | AAA | GTT | GAA | GAT | CTC | AGT | AAG | GTA | GGG | CGA | TCA | GTT | AGC | 3957 |
|---|---|---|---|---|---|---|---|---|---|---|---|---|---|---|---|---|
| Arg | His | Asp | Lys | Val | Glu | Asp | Leu | Ser | Lys | Val | Gly | Arg | Ser | Val | Ser |   |
|   |   |   | 950 |   |   |   |   | 955 |   |   |   |   | 960 |   |   |   |

| CCT | GAA | CCC | ATT | TAT | GCT | ACA | ATT | GAT | GAT | CTC | GGT | GGG | TCT | TTC | CCT | 4005 |
|---|---|---|---|---|---|---|---|---|---|---|---|---|---|---|---|---|
| Pro | Glu | Pro | Ile | Tyr | Ala | Thr | Ile | Asp | Asp | Leu | Gly | Gly | Ser | Phe | Pro |   |
|   |   | 965 |   |   |   |   | 970 |   |   |   |   | 975 |   |   |   |   |

| TTG | AAA | AGG | CAT | GAT | AAA | GTT | GAT | GAT | CTC | AGT | AAG | GTA | GGG | CTT | TCA | 4053 |
|---|---|---|---|---|---|---|---|---|---|---|---|---|---|---|---|---|
| Leu | Lys | Arg | His | Asp | Lys | Val | Asp | Asp | Leu | Ser | Lys | Val | Gly | Leu | Ser |   |
|   | 980 |   |   |   |   | 985 |   |   |   |   | 990 |   |   |   |   |   |

| AGG | AAT | CAA | GAA | TTG | ACT | CAG | AAA | ATT | GAC | AAT | CTC | AGT | CAA | GCG | GTA | 4101 |
|---|---|---|---|---|---|---|---|---|---|---|---|---|---|---|---|---|
| Arg | Asn | Gln | Glu | Leu | Thr | Gln | Lys | Ile | Asp | Asn | Leu | Ser | Gln | Ala | Val |   |
| 995 |   |   |   |   | 1000 |   |   |   |   | 1005 |   |   |   |   | 1010 |   |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| TCA | GAA | GCT | AAA | GCA | GGT | TTT | TTT | GGC | AAT | CTA | GAA | CAA | ACG | ATA | GAC | 4149 |
| Ser | Glu | Ala | Lys | Ala | Gly | Phe | Phe | Gly | Asn | Leu | Glu | Gln | Thr | Ile | Asp |      |
|     |     |     | 1015 |    |     |     |     |     | 1020 |    |     |     |     | 1025 |    |      |
| AAG | CTC | AAA | GAT | TTT | ACA | AAA | AAC | AAT | CCT | GTG | AAT | CTA | TGG | GCT | GAA | 4197 |
| Lys | Leu | Lys | Asp | Phe | Thr | Lys | Asn | Asn | Pro | Val | Asn | Leu | Trp | Ala | Glu |      |
|     |     |     | 1030 |    |     |     |     |     | 1035 |    |     |     |     | 1040 |    |      |
| AGC | GCA | AAA | AAA | GTG | CCT | GCT | AGT | TTG | TCA | GCG | AAA | CTA | GAC | AAT | TAC | 4245 |
| Ser | Ala | Lys | Lys | Val | Pro | Ala | Ser | Leu | Ser | Ala | Lys | Leu | Asp | Asn | Tyr |      |
|     |     |     | 1045 |    |     |     |     |     | 1050 |    |     |     |     | 1055 |    |      |
| GCT | ACT | AAC | AGC | CAC | ACA | CGC | ATT | AAT | AGC | AAT | ATC | CAA | AAT | GGA | GCG | 4293 |
| Ala | Thr | Asn | Ser | His | Thr | Arg | Ile | Asn | Ser | Asn | Ile | Gln | Asn | Gly | Ala |      |
|     |     |     | 1060 |    |     |     |     |     | 1065 |    |     |     |     | 1070 |    |      |
| ATC | AAT | GAA | AAA | GCG | ACC | GGC | ACT | GAA | CGG | CAA | AAA | AAC | CCT | GAG | TGG | 4341 |
| Ile | Asn | Glu | Lys | Ala | Thr | Gly | Thr | Glu | Arg | Gln | Lys | Asn | Pro | Glu | Trp |      |
| 1075 |    |     |     |     | 1080 |    |     |     |     | 1085 |    |     |     |     | 1090 |      |
| CTC | AAA | CTC | GTG | AAT | GAT | AAG | ATC | GTT | GCG | CAT | AAT | GTG | GGA | AGC | GTT | 4389 |
| Leu | Lys | Leu | Val | Asn | Asp | Lys | Ile | Val | Ala | His | Asn | Val | Gly | Ser | Val |      |
|     |     |     |     | 1095 |    |     |     |     | 1100 |    |     |     |     | 1105 |    |      |
| CCT | TTG | TCA | GAG | TAT | GAT | AAC | ATT | GGA | TTC | AGC | CAA | AAG | AAT | ATG | AAG | 4437 |
| Pro | Leu | Ser | Glu | Tyr | Asp | Asn | Ile | Gly | Phe | Ser | Gln | Lys | Asn | Met | Lys |      |
|     |     |     | 1110 |    |     |     |     |     | 1115 |    |     |     |     | 1120 |    |      |
| GAT | TAT | TCT | GAT | TCG | TTC | AAG | TTT | TCC | ACC | AAG | TTG | AAC | AAT | GCC | GTA | 4485 |
| Asp | Tyr | Ser | Asp | Ser | Phe | Lys | Phe | Ser | Thr | Lys | Leu | Asn | Asn | Ala | Val |      |
|     |     |     | 1125 |    |     |     |     |     | 1130 |    |     |     |     | 1135 |    |      |
| AAA | GAC | ATT | AAG | TCT | GGC | TTT | ACG | CAA | TTT | TTA | GCC | AAT | GCA | TTT | TCT | 4533 |
| Lys | Asp | Ile | Lys | Ser | Gly | Phe | Thr | Gln | Phe | Leu | Ala | Asn | Ala | Phe | Ser |      |
|     |     |     | 1140 |    |     |     |     |     | 1145 |    |     |     |     | 1150 |    |      |
| ACA | GGA | TAT | TAC | TCC | ATG | GCG | AGA | GAA | AAT | GCG | GAG | CAT | GGA | ATC | AAA | 4581 |
| Thr | Gly | Tyr | Tyr | Ser | Met | Ala | Arg | Glu | Asn | Ala | Glu | His | Gly | Ile | Lys |      |
| 1155 |    |     |     |     | 1160 |    |     |     |     | 1165 |    |     |     |     | 1170 |      |
| AAT | GCT | AAT | ACA | AAA | GGT | GGT | TTC | CAA | AAA | TCT | TAAGGATTA | AGGAACACCA | 4634 |
| Asn | Ala | Asn | Thr | Lys | Gly | Gly | Phe | Gln | Lys | Ser |     |     |     |     |     |      |
|     |     |     | 1175 |    |     |     |     |     | 1180 |    |     |     |     |     |     |      |

| | |
|---|---|
| AAAACGCAAA AACCACCTTG CTAAAAGCAA GGGGTTTTTT AACTTAAAAT ATCCCGACAG | 4694 |
| ACACTAACGA AAGGCTTTGT TCTTTAAAGT CTGCATAGAT ATTTCCTACC CCAAAAAGAC | 4754 |
| TTAACCCTTT GCTTAAAATT AAATTTGATT GTGCTAGTGG GTTCGTGCTT TATAGTGCGG | 4814 |
| AATTGGG | 4821 |

( 2 ) INFORMATION FOR SEQ ID NO:4:

( i ) SEQUENCE CHARACTERISTICS:
        ( A ) LENGTH: 1181 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

|     |     |     |     |     |     |     |     |     |     |     |     |     |     |     |
|-----|-----|-----|-----|-----|-----|-----|-----|-----|-----|-----|-----|-----|-----|-----|
| Met | Thr | Asn | Glu | Thr | Ile | Asp | Gln | Gln | Pro | Gln | Thr | Glu | Ala | Ala | Phe |
| 1   |     |     |     | 5   |     |     |     |     | 10  |     |     |     |     | 15  |
| Asn | Pro | Gln | Gln | Phe | Ile | Asn | Asn | Leu | Gln | Val | Ala | Phe | Leu | Lys | Val |
|     |     |     | 20  |     |     |     |     | 25  |     |     |     |     | 30  |     |
| Asp | Asn | Ala | Val | Ala | Ser | Tyr | Asp | Pro | Asp | Gln | Lys | Pro | Ile | Val | Asp |
|     |     | 35  |     |     |     |     | 40  |     |     |     |     | 45  |     |     |
| Lys | Asn | Asp | Arg | Asp | Asn | Arg | Gln | Ala | Phe | Glu | Gly | Ile | Ser | Gln | Leu |
|     | 50  |     |     |     |     | 55  |     |     |     |     | 60  |     |     |     |
| Arg | Glu | Glu | Tyr | Ser | Asn | Lys | Ala | Ile | Lys | Asn | Pro | Thr | Lys | Lys | Asn |
| 65  |     |     |     |     | 70  |     |     |     |     | 75  |     |     |     |     | 80  |
| Gln | Tyr | Phe | Ser | Asp | Phe | Ile | Asn | Lys | Ser | Asn | Asp | Leu | Ile | Asn | Lys |
|     |     |     |     | 85  |     |     |     |     | 90  |     |     |     |     | 95  |

| | | | | | | | | | | | | | |
|---|---|---|---|---|---|---|---|---|---|---|---|---|---|
|Asp|Asn|Leu|Ile 100|Val|Val|Glu|Ser|Ser 105|Thr|Lys|Ser|Phe|Gln 110|Lys|Phe|
|Gly|Asp|Gln 115|Arg|Tyr|Arg|Ile|Phe 120|Thr|Ser|Trp|Val|Ser 125|His|Gln|Asn|
|Asp|Pro 130|Ser|Lys|Ile|Asn|Thr 135|Arg|Cys|Ile|Arg|Asn 140|Phe|Met|Glu|His|
|Thr 145|Ile|Gln|Pro|Pro|Ile 150|Pro|Asp|Asp|Lys|Glu 155|Lys|Ala|Glu|Phe|Leu 160|
|Lys|Ser|Ala|Lys|Gln 165|Ser|Phe|Ala|Gly|Ile 170|Ile|Ile|Gly|Asn|Gln 175|Ile|
|Arg|Thr|Asp|Gln 180|Lys|Phe|Met|Gly|Val 185|Phe|Asp|Glu|Ser|Leu 190|Lys|Glu|
|Arg|Gln|Glu 195|Ala|Glu|Lys|Asn|Gly 200|Gly|Pro|Thr|Gly|Gly 205|Asp|Trp|Leu|
|Asp|Ile 210|Phe|Leu|Ser|Phe|Ile 215|Phe|Asp|Lys|Lys|Gln 220|Ser|Ser|Asp|Val|
|Lys 225|Glu|Ala|Ile|Asn|Gln 230|Glu|Pro|Leu|Pro|His 235|Val|Gln|Pro|Asp|Ile 240|
|Ala|Thr|Ser|Thr|Thr 245|His|Ile|Gln|Gly|Leu 250|Pro|Pro|Glu|Ser|Arg 255|Asp|
|Leu|Leu|Asp|Glu 260|Arg|Gly|Asn|Phe|Ser 265|Lys|Phe|Thr|Leu|Gly 270|Asp|Met|
|Glu|Met|Leu 275|Asp|Val|Glu|Gly|Val 280|Ala|Asp|Met|Asp|Pro 285|Asn|Tyr|Lys|
|Phe|Asn 290|Gln|Leu|Leu|Ile|His 295|Asn|Asn|Thr|Leu|Ser 300|Ser|Val|Leu|Met|
|Gly 305|Ser|His|Asp|Gly|Ile 310|Glu|Pro|Glu|Lys|Val 315|Ser|Leu|Leu|Tyr|Ala 320|
|Gly|Asn|Gly|Gly|Phe 325|Gly|Ala|Lys|His|Asp 330|Trp|Asn|Ala|Thr|Val 335|Gly|
|Tyr|Lys|Asp|Gln 340|Gln|Gly|Asn|Asn|Val 345|Ala|Thr|Ile|Ile|Asn 350|Val|His|
|Met|Lys|Asn 355|Gly|Ser|Gly|Leu|Val 360|Ile|Ala|Gly|Gly|Glu 365|Lys|Gly|Ile|
|Asn|Asn 370|Pro|Ser|Phe|Tyr|Leu 375|Tyr|Lys|Glu|Asp|Gln 380|Leu|Thr|Gly|Ser|
|Gln 385|Arg|Ala|Leu|Ser|Gln 390|Glu|Glu|Ile|Gln|Asn 395|Lys|Ile|Asp|Phe|Met 400|
|Glu|Phe|Leu|Ala|Gln 405|Asn|Asn|Ala|Lys|Leu 410|Asp|Ser|Leu|Ser|Glu 415|Lys|
|Glu|Lys|Glu|Lys 420|Phe|Arg|Asn|Glu|Ile 425|Lys|Asp|Phe|Gln|Lys 430|Asp|Ser|
|Lys|Pro|Tyr 435|Leu|Asp|Ala|Leu|Gly 440|Asn|Asp|Arg|Ile|Ala 445|Phe|Val|Ser|
|Lys|Lys 450|Asp|Pro|Lys|His|Ser 455|Ala|Leu|Ile|Thr|Glu 460|Phe|Asn|Lys|Gly|
|Asp 465|Leu|Ser|Tyr|Thr|Leu 470|Lys|Val|Met|Gly|Lys 475|Lys|Gln|Ile|Lys|Ala 480|
|Leu|Asp|Arg|Glu|Lys 485|Asn|Val|Thr|Leu|Gln 490|Gly|Asn|Leu|Lys|His 495|Asp|
|Gly|Val|Met|Phe 500|Val|Asn|Tyr|Ser|Asn 505|Phe|Lys|Tyr|Thr|Asn 510|Ala|Ser|
|Lys|Ser|Pro 515|Asn|Lys|Gly|Val|Gly 520|Val|Thr|Asn|Gly|Val 525|Ser|His|Leu|

-continued

| | | | | | | | | | | | | | |
|---|---|---|---|---|---|---|---|---|---|---|---|---|---|
|Glu|Ala|Gly|Phe|Ser|Lys|Val|Ala|Val|Phe|Asn|Leu|Pro|Asn|Leu|Asn|
| |530| | | |535| | | |540| | | | | |
|Asn|Leu|Ala|Ile|Thr|Ser|Val|Val|Arg|Arg|Asp|Leu|Glu|Asp|Lys|Leu|
|545| | | | |550| | | |555| | | | |560|
|Ile|Ala|Lys|Gly|Leu|Ser|Pro|Gln|Glu|Ala|Asn|Lys|Leu|Val|Lys|Asp|
| | | | |565| | | |570| | | | |575| |
|Phe|Leu|Ser|Ser|Asn|Lys|Glu|Leu|Val|Gly|Lys|Ala|Leu|Asn|Phe|Asn|
| | | |580| | | | |585| | | | |590| | |
|Lys|Ala|Val|Ala|Glu|Ala|Lys|Asn|Thr|Gly|Asn|Tyr|Asp|Glu|Val|Lys|
| | |595| | | |600| | | |605| | | | |
|Arg|Ala|Gln|Lys|Asp|Leu|Glu|Lys|Ser|Leu|Lys|Lys|Arg|Glu|His|Leu|
| |610| | | | |615| | | |620| | | | |
|Glu|Lys|Asp|Val|Ala|Lys|Asn|Leu|Glu|Ser|Lys|Ser|Gly|Asn|Lys|Asn|
|625| | | |630| | | |635| | | | | |640|
|Lys|Met|Glu|Ala|Lys|Ala|Gln|Ala|Asn|Ser|Gln|Lys|Asp|Glu|Ile|Phe|
| | | |645| | | |650| | | | |655| | |
|Ala|Leu|Ile|Asn|Lys|Glu|Ala|Asn|Arg|Asp|Ala|Arg|Ala|Ile|Ala|Tyr|
| | |660| | | | |665| | | |670| | | |
|Ala|Gln|Asn|Leu|Lys|Gly|Ile|Lys|Arg|Glu|Leu|Ser|Asp|Lys|Leu|Glu|
| | |675| | | | |680| | | |685| | | |
|Asn|Ile|Asn|Lys|Asp|Leu|Lys|Asp|Phe|Ser|Lys|Ser|Phe|Asp|Gly|Phe|
| |690| | | |695| | | |700| | | | | |
|Lys|Asn|Gly|Lys|Asn|Lys|Asp|Phe|Ser|Lys|Ala|Glu|Glu|Thr|Leu|Lys|
|705| | | |710| | | |715| | | | | |720|
|Ala|Leu|Lys|Gly|Ser|Val|Lys|Asp|Leu|Gly|Ile|Asn|Pro|Glu|Trp|Ile|
| | | |725| | | |730| | | | |735| |
|Ser|Lys|Val|Glu|Asn|Leu|Asn|Ala|Ala|Leu|Asn|Glu|Phe|Lys|Asn|Gly|
| | | |740| | | |745| | | | |750| | |
|Lys|Asn|Lys|Asp|Phe|Ser|Lys|Val|Thr|Gln|Ala|Lys|Ser|Asp|Gln|Glu|
| | |755| | | | |760| | | |765| | | |
|Asn|Ser|Ile|Lys|Asp|Val|Ile|Ile|Asn|Gln|Lys|Ile|Thr|Asp|Lys|Val|
| |770| | | | |775| | | |780| | | | |
|Asp|Glu|Leu|Asn|Gln|Ala|Val|Ser|Val|Ala|Lys|Ile|Ala|Cys|Asp|Phe|
|785| | | |790| | | |795| | | | | |800|
|Ser|Gly|Val|Glu|Gln|Ala|Leu|Ala|Asp|Leu|Lys|Asn|Phe|Ser|Lys|Glu|
| | | |805| | | |810| | | | |815| |
|Gln|Leu|Ala|Gln|Gln|Ala|Gln|Lys|Asn|Glu|Ser|Phe|Asn|Val|Gly|Lys|
| | |820| | | | |825| | | |830| | | |
|Ser|Glu|Ile|Tyr|Gln|Ser|Val|Lys|Asn|Gly|Val|Asn|Gly|Thr|Leu|Val|
| | |835| | | |840| | | |845| | | |
|Gly|Asn|Gly|Leu|Ser|Gly|Ile|Glu|Ala|Thr|Ala|Leu|Ala|Lys|Asn|Phe|
| |850| | | |855| | | |860| | | | |
|Ser|Asp|Ile|Lys|Lys|Glu|Leu|Asn|Glu|Lys|Phe|Lys|Asn|Phe|Asn|Asn|
|865| | | |870| | | |875| | | | |880|
|Asn|Asn|Asn|Asn|Gly|Leu|Lys|Asn|Gly|Glu|Pro|Ile|Tyr|Ala|Gln|
| | | |885| | | |890| | | |895| |
|Val|Asn|Lys|Lys|Lys|Thr|Gly|Gln|Val|Ala|Ser|Pro|Glu|Glu|Pro|Ile|
| | |900| | | |905| | | |910| | |
|Tyr|Ala|Gln|Val|Ala|Lys|Lys|Val|Thr|Lys|Lys|Ile|Asp|Gln|Leu|Asn|
| |915| | | | |920| | | |925| | | |
|Gln|Ala|Ala|Thr|Ser|Gly|Phe|Gly|Gly|Val|Gly|Gln|Ala|Gly|Phe|Pro|
|930| | | | |935| | | | |940| | | |
|Leu|Lys|Arg|His|Asp|Lys|Val|Glu|Asp|Leu|Ser|Lys|Val|Gly|Arg|Ser|
|945| | | |950| | | |955| | | | |960|
|Val|Ser|Pro|Glu|Pro|Ile|Tyr|Ala|Thr|Ile|Asp|Asp|Leu|Gly|Gly|Ser|

|   |   |   |   |   | 965 |   |   |   | 970 |   |   |   | 975 |   |
|---|---|---|---|---|---|---|---|---|---|---|---|---|---|---|
| Phe | Pro | Leu | Lys 980 | Arg | His | Asp | Lys | Val 985 | Asp | Asp | Leu | Ser | Lys 990 | Val | Gly |
| Leu | Ser | Arg 995 | Asn | Gln | Glu | Leu | Thr 1000 | Gln | Lys | Ile | Asp | Asn 1005 | Leu | Ser | Gln |
| Ala | Val | Ser 1010 | Glu | Ala | Lys | Ala | Gly 1015 | Phe | Phe | Gly | Asn | Leu 1020 | Glu | Gln | Thr |
| Ile 1025 | Asp | Lys | Leu | Lys | Asp 1030 | Phe | Thr | Lys | Asn | Asn 1035 | Pro | Val | Asn | Leu | Trp 1040 |
| Ala | Glu | Ser | Ala | Lys 1045 | Lys | Val | Pro | Ala | Ser 1050 | Leu | Ser | Ala | Lys 1055 | Leu | Asp |
| Asn | Tyr | Ala | Thr 1060 | Asn | Ser | His | Thr | Arg 1065 | Ile | Asn | Ser | Asn 1070 | Ile | Gln | Asn |
| Gly | Ala | Ile | Asn 1075 | Glu | Lys | Ala | Thr 1080 | Gly | Thr | Glu | Arg | Gln 1085 | Lys | Asn | Pro |
| Glu | Trp 1090 | Leu | Lys | Leu | Val | Asn 1095 | Asp | Lys | Ile | Val | Ala 1100 | His | Asn | Val | Gly |
| Ser | Val 1105 | Pro | Leu | Ser | Glu 1110 | Tyr | Asp | Asn | Ile | Gly 1115 | Phe | Ser | Gln | Lys | Asn 1120 |
| Met | Lys | Asp | Tyr | Ser 1125 | Asp | Ser | Phe | Lys | Phe 1130 | Ser | Thr | Lys | Leu | Asn 1135 | Asn |
| Ala | Val | Lys | Asp 1140 | Ile | Lys | Ser | Gly | Phe 1145 | Thr | Gln | Phe | Leu | Ala 1150 | Asn | Ala |
| Phe | Ser | Thr 1155 | Gly | Tyr | Tyr | Ser | Met 1160 | Ala | Arg | Glu | Asn | Ala 1165 | Glu | His | Gly |
| Ile | Lys 1170 | Asn | Ala | Asn | Thr | Lys 1175 | Gly | Gly | Phe | Gln | Lys 1180 | Ser |